(12) United States Patent
Wang et al.

(10) Patent No.: US 10,525,143 B2
(45) Date of Patent: Jan. 7, 2020

(54) CONJUGATE OF POLYETHYLENE GLYCOL AND ANESTHETIC, AND PREPARATION METHOD THEREOF

(71) Applicant: JenKem Technology Co., Ltd. (Tianjin), Tianjin (CN)

(72) Inventors: Jinliang Wang, Tianjin (CN); Zewang Feng, Tianjin (CN); Hui Zhu, Tianjin (CN); Meina Lin, Tianjin (CN); Yan Liu, Tianjin (CN); Xuan Zhao, Tianjin (CN)

(73) Assignee: JENKEM TECHNOLOGY CO., LTD. (TIANJIN), Tianjin (CN)

( * ) Notice: Subject to any disclaimer, the term of this patent is extended or adjusted under 35 U.S.C. 154(b) by 7 days.

(21) Appl. No.: 15/848,987

(22) Filed: Dec. 20, 2017

(65) Prior Publication Data

US 2018/0110867 A1 Apr. 26, 2018

Related U.S. Application Data

(63) Continuation of application No. PCT/CN2016/085681, filed on Jun. 14, 2016.

(30) Foreign Application Priority Data

Jun. 24, 2015 (CN) .......................... 2015 1 0354709

(51) Int. Cl.

| | | |
|---|---|---|
| *A61K 47/60* | (2017.01) | |
| *A61K 9/06* | (2006.01) | |
| *A61K 9/08* | (2006.01) | |
| *A61K 9/20* | (2006.01) | |
| *A61K 9/70* | (2006.01) | |
| *A61K 47/10* | (2017.01) | |
| *A61K 47/18* | (2017.01) | |
| *A61K 9/14* | (2006.01) | |
| *A61K 9/48* | (2006.01) | |

(52) U.S. Cl.
CPC ................ *A61K 47/60* (2017.08); *A61K 9/06* (2013.01); *A61K 9/08* (2013.01); *A61K 9/148* (2013.01); *A61K 9/20* (2013.01); *A61K 9/70* (2013.01); *A61K 47/10* (2013.01); *A61K 47/186* (2013.01)

(58) Field of Classification Search
CPC . A61K 47/60; A61K 9/06; A61K 9/08; A61K 9/20; A61K 9/48; A61K 9/70; A61K 47/10; A61K 47/186
See application file for complete search history.

(56) References Cited

U.S. PATENT DOCUMENTS

2018/0110867 A1* 4/2018 Wang .................... A61K 47/60

FOREIGN PATENT DOCUMENTS

| CN | 108727208 | * 11/2018 |
|---|---|---|
| WO | WO2018121427 | * 7/2018 |

* cited by examiner

*Primary Examiner* — Johann R Richter
*Assistant Examiner* — Genevieve S Alley
(74) *Attorney, Agent, or Firm* — Flener IP & Business Law; Zareefa B. Flener

(57) ABSTRACT

A conjugate represented by general formula (I), wherein $R_0$ is a $C_{1-6}$ alkyl, B is an anesthetic, and A is a linking group, and a quaternary ammonium salt is formed at the linking position between B and $R_0$. The conjugate has a prolonged analgesic effect, and can be used in postoperative analgesia or treatment for chronic pain.

20 Claims, No Drawings

CONJUGATE OF POLYETHYLENE GLYCOL AND ANESTHETIC, AND PREPARATION METHOD THEREOF

CROSS-REFERENCE TO RELATED APPLICATION

This application is a continuation application of International patent application No. PCT/CN2016/085681, filed on Jun. 14, 2016, which claims the benefit and priority of Chinese patent application No. CN201510354709.6, filed on Jun. 24, 2015, each of which is incorporated herein by reference in its entirety and for all purposes.

FIELD OF THE INVENTION

The present invention relates to a conjugate of polyethylene glycol and anesthetic and preparation and application thereof, belonging to the field of medical technology, in particular to a conjugate of polyethylene glycol and local anesthetic through a linker and preparation and application thereof.

BACKGROUND OF THE INVENTION

Chronic pain, especially postoperative pain, is a common clinical symptom, involving diseases including various clinical diseases, may produce a series of pathophysiological changes while making the patient feel painful, such as affecting the body's autonomic nervous system, resulting in an accelerated heart rate, hard and jerky breath, and risen blood pressure; affecting the mood, resulting in dysphoria and depression, followed by affecting the digestive system function and physical recovery; affecting the endocrine and hormone levels, disrupting the body's internal environment directly and indirectly. Therefore, a reasonable analgesia should play the role of: (1) alleviating the sufferer's pain and discomfort, relieving anxiety, and improving sleep; allowing the patient to pass the postoperative stage in a more comfortable state; (2) eliminating symptoms of not wishing to breathe deeply and coughing caused by pain, improving breathing, promoting sputum excretion, reducing lung infection; (3) alleviating pain, promoting patients to leave bed and move early, early functional exercise, reducing the risk of deep venous thrombosis caused by staying in bed for long periods of time; (4) blocking the sympathetic overexcitation, eliminating tension, expanding the blood vessel, improving the microcirculation, thereby promoting wound healing, and speeding up the postoperative recovery; (5) inhibiting sympathetic activity, promoting gastrointestinal motility, helping restore gastrointestinal function after surgery; and, (6) shortening the hospitalization time and saving the cost by reducing the complications and accelerating the rehabilitation.

Many primary symptoms of chronic pain are not easy to be eliminated, and the pain symptoms caused by them are mostly treated by symptomatic treatment. Local block therapy is usually used, especially local anesthetic is used. They can temporarily block the nerve conduction completely and reversibly within the limited range of the human body, that is, make a certain part of the human body loss sensibility without the disappearance of consciousness, and thus play a role in relieving pain. For example, bupivacaine may be used alone or in combination with fentanyl or morphine for postoperative patient controlled epidural analgesia.

Local anesthesia is commonly used in clinical anesthesia, which is conducive to keeping the patient awake, smooth recovery of anesthesia, and easy postoperative analgesia. According to the structure type, local anesthetics can be divided into p-aminobenzoates, amides, aminoketones, amino ethers, and carbamates. The commonly used drugs are lidocaine, prilocaine, bupivacaine and ropivacaine, etc. In general, the local anesthetic has an activity sufficient to relieve certain pain, however the duration thereof is not long enough, and the patients are more likely to consistently input a low concentration of local anesthetic, to block only pain nerve without affecting the motor nerve, so as to achieve the goal of only playing analgesic effect without affecting the movement. Therefore, a sustained-release and long-acting local anesthetic is an ideal choice. Structural modification of the original local anesthetics is a way to prolong the duration of local anesthesia. E.g., bupivacaine has a structure similar to lidocaine, effect of local anesthesia stronger than that of lidocaine, and longer duration; L-bupivacaine is a new long-acting local anesthetic, as an isomer of bupivacaine, has a relatively low toxicity. Ropivacaine is structurally similar to bupivacaine, has a stronger effect for blocking the pain and has a weaker effect on exercise. In recent years, the development of peripheral nerve block technology and local anesthetic provides patients with more ideal and effective method of perioperative analgesia, usually combined with opioids, which can reduce the amount of opioids. Local anesthetics of amides such as bupivacaine, L-bupivacaine and ropivacaine are widely used in regional analgesia, especially ropivacaine, has the characteristics of separated blockade of sensory and motor, making them the preferred drug for regional analgesia. However, the duration of these drugs is still too low for the treatment of postoperative analgesia or chronic pain, e.g., the duration of lidocaine is 1-2 h, the duration of ropivacaine is 4.4 h, and even the duration of L-bupivacaine which is a long-acting local anesthetic is only 5-7 h.

Several sustained-release formulations of local anesthetic developed at present have been reported, e.g., polymer microspheres of polylactic acid combined with glycolic acid containing bupivacaine and dexamethasone can produce local anesthesia effect with long duration. The crystals of local anesthetics have also been shown to have a long duration. Lipophilic bupivacaine free radicals are incorporated into a multilayer liposomal cell membrane, and proton-gradient-loaded huge monolayer liposomes have been shown to last for 6-11 h. Multivesicular liposomes are being developed as a lipid-based topical or systemic slow-release drug. In November 2011, the FDA approved the Exparel, 1.3% liposome suspension for injection of bupivacaine developed by Pacira Pharmaceutical Co., Ltd., which was used for direct injection to the surgical site to help control postoperative pain. Bupivacaine is a non-opioid anesthetic, its conventional injection (0.5%) can only provide analgesic effect for less than 7 h, and postoperative pain may often last 48-72 h and is the most difficult to control in this time, so now a built-in catheter or infusion pump is usually used for continuous administration of opioids, resulting in management inconvenience and a variety of harmful side effects which may appear. By contrast, a single dose of Exparel can produce a significant analgesic effect up to 72 h after being injected into the surgical site, and thus reduce opioid dosage, which can be regarded as an important progress of postoperative pain management.

SUMMARY OF THE INVENTION

It is an object of the present invention to provide a conjugate of polyethylene glycol and anesthetic and preparation and application thereof, in which the drug takes polyethylene glycol as a carrier to allow the drug to remain in the lesion location for a long period of time, and then by degradation of the drug from the conjugate chain, the purpose of sustained release and controlled release can be achieved.

It is another object of the present invention to provide a pharmaceutical composition comprising the conjugate of the present invention and a pharmaceutically acceptable carrier or excipient.

It is a further object of the present invention to provide an application of the conjugate and pharmaceutical composition thereof for the manufacture of a medication for analgesia or treatment of chronic pain.

In order to realize the object of the present invention, the following technical scheme is adopted by the present invention:

In one aspect, the present invention provides a conjugate of polyethylene glycol and anesthetic having the structure of formula (I):

$$PEG-A-R_0-B \quad (I)$$

wherein, PEG is polyethylene glycol residue with a molecular weight of 1-100 KDa;

$R_0$ is a $C_{1-6}$ alkyl, preferably, $R_0$ is methyl, ethyl or propyl, more preferably, $R_0$ is methyl;

B is an anesthetic, preferably, B is a local anesthetic;

a quaternary ammonium salt with a structure of $$-\overset{|}{\underset{|}{N^+}}-R^{s0-}$$

is formed at the linking position between B and $R_0$, $R^{s0-}$ is selected from the group consisting of F—, Cl—, Br—, I—, methanesulfonate, ethanesulfonate, benzenesulfonate, citrate, lactate, succinate, fumarate, glutamate, citrate, salicylate, and maleate, preferably, $R^{s0-}$ is selected from the group consisting of F—, Cl—, Br—, I—, methanesulfonate, ethanesulfonate, and benzenesulfonate; most preferably, $R^{s0-}$ is selected from the group consisting of F—, Cl—, Br—, and I—;

and, A is a linking group selected from the group consisting of the structures shown by the following formula $A_1$ or $A_2$:

(A₁) [structure showing $R_{20}-R_1$ with $R_2$, $R_3$ attached to benzene ring with $R_4$, $R_5$ substituents]

(A₂) [structure showing $R_{20}-R_6-R_7$ with benzene ring bearing $R_8$, $R_9$ substituents]

wherein, $R_1$ and $R_6$ are independently selected from $C_{1-6}$ alkyl, preferably methyl, ethyl, or propyl, or $R_1$ and $R_6$ are independently selected from $-(CH_2)_iNHCO(CH_2)_j-$, and $-(CH_2)_iCONH(CH_2)_j-$, i and j are integer independently selected from 0 to 6, preferably 1, 2, or 3;

$R_2$ is selected from the group consisting of $-C=O$, $-C=S$, $-O-$ or $-S-$, preferably $-C=O$, $-O-$ or $-S-$;

$R_3$ and $R_7$ are independently selected from the group consisting of $-O-$ or $-S-$;

$R_4$ or $R_5$ is independently selected from the group consisting of H, $C_{1-6}$ alkyl or halogen (F, Cl, Br, and I), preferably H, methyl or ethyl, most preferably H or methyl;

$R_8$ or $R_9$ is independently selected from the group consisting of H, $C_{1-6}$ alkyl or $-O(C=O)(CH_2)_iCH_3$, with i being an integer selected from 0 to 6, preferably 1, 2, or 3, preferably H, methyl, ethyl, propyl, acetoxy, propionyloxy, and butyryloxy; most preferably $R_8$ is acetoxy, propionyloxy or butyryloxy, $R_9$ is H or methyl;

and, $R_{20}$ is

[structure of triazole ring with $R^{s1}$ substituent]

$R^{s1}$ is selected from the group consisting of H or $C_{1-6}$ alkyl, preferably H, methyl, ethyl or propyl. In the present invention, $R_1$ or $R_6$ may be attached to the carbon atom in the five-membered ring of $R_{20}$ and may also be attached to the nitrogen atom in the five-membered ring of $R_{20}$.

The PEG of the present invention is a linear or branched PEG (2- to 10-arm branched PEG) comprising linear PEG, double-ended PEG, 2-arm branched PEG, 4-arm branched PEG, 6-arm branched PEG or 8-arm branched PEG and the like, PEG has a molecular weight of 1 to 100 KDa, e.g., 1 to 10 KDa (specifically, 1, 2, 3, 4, 5, 6, 7, 8, 9, or 10 KDa), 10 to 50 KDa (specifically, 10, 15, 20, 25, 30, 35, 40, 45, or 50 KDa), 50 to 100 KDa (specifically, 50, 55, 60, 65, 70, 75, 80, 85, 90, 95, or 100 KDa); preferably, PEG has a molecular weight of 10 to 50 KDa, most preferably 10 to 40 KDa, e.g., between 10 KDa and 20 KDa, between 20 KDa and 25 KDa, between 25 KDa and 30 KDa, between 30 KDa and 35 KDa, and between 35 KDa and 40 KDa.

In some embodiments, the PEG may be a linear, double-ended, Y-type or multi-branched polyethylene glycol residue.

Preferably, the PEG is a linear polyethylene glycol residue having the structure of formula (II-1):

(II-1) [structure of linear PEG: $-O-(CH_2CH_2O)_m-$]

wherein, m is a positive integer of 200 to 1000, such as 200, 250, 300, 450, 600, and the like.

When the PEG is a Y-type polyethylene glycol, it has the structure of formula (II-2):

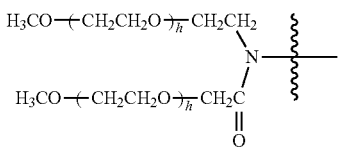
(II-2)

wherein, h is an integer of 10 to 1000, preferably, h is an integer of 100 to 500. When the PEG is a multi-branched polyethylene glycol, it has the structures of formula (II-3) to formula (II-5):

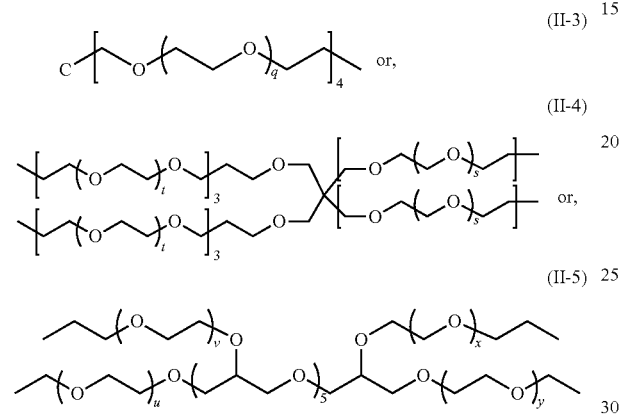

(II-3)

(II-4)

(II-5)

wherein, q is an integer selected from 5 to 500, preferably q is an integer of 50 to 250;

s, t, u, v, x, and y are integer independently selected from 2 to 250, preferably, s, t, u, v, x, and y are integer independently selected from 25 to 125.

The use of Y-type or multi-branched polyethylene glycol can increase the loading of the drug to ensure proper drug concentration and enhanced sustained release. When a Y-type or multi-branched polyethylene glycol residue is employed, one or more arms of the multi-branched polyethylene glycol may optionally be attached to one or more linking groups, correspondingly loaded with more drugs.

In some embodiments, the linking group A of the present invention is selected from the group consisting of the structures shown in the following formulas $A_3$-$A_6$:

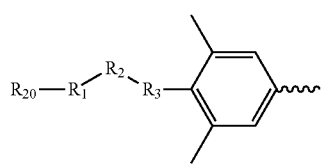
(A3)

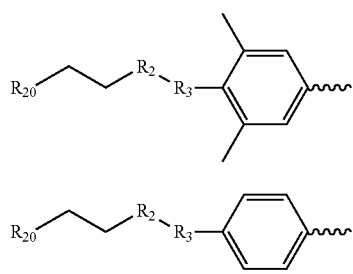
(A4)

(A5)

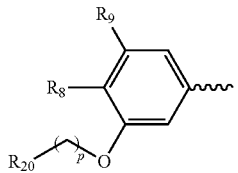
(A6)

wherein, $R_1$ is methyl, ethyl, propyl or —(CH$_2$)iNHCO(CH$_2$)j-, (CH$_2$)iCONH(CH$_2$)j-, i and j are independently selected from 1, 2 or 3;

$R_2$ is —C=O, —O— or —S—;

$R_3$ is —O— or —S—;

$R_8$ is acetoxy, propionyloxy or butyryloxy;

$R_9$ is H or methyl;

$R_{20}$ is

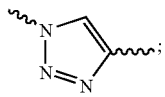

and, P is 1, 2 or 3.

In some embodiments, the anesthetic of the present invention is a local anesthetic of amides having the structure of formula (III):

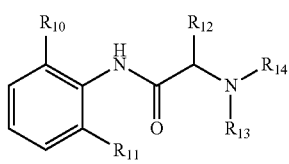
(III)

wherein, $R_{10}$ and $R_{11}$ are independently selected from the group consisting of H and $C_{1-6}$ alkyl, preferably H, methyl, ethyl or propyl;

and, $R_{12}$, $R_{13}$ and $R_{14}$ are independently selected from the group consisting of H and $C_{1-6}$ alkyl, preferably H, methyl, ethyl, propyl or butyl; or $R_{13}$ is selected from the group consisting of H and $C_{1-6}$ alkyl, N together with $R_{12}$ and $R_{14}$ forms a 5- to 8-membered ring, preferably a 6-membered ring.

Preferably, the anesthetic may be lidocaine, prilocaine, bupivacaine, ropivacaine, mepivacaine or etidocaine etc.

In some embodiments, the conjugate has a structure of following formula (IV):

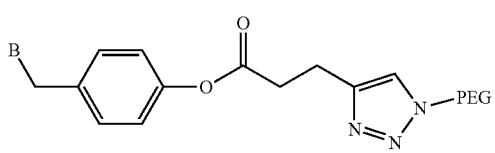
(IV)

wherein, a quaternary ammonium salt with a structure of

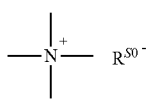

is formed at the linking position between B and —CH$_2$—, and, R$^{s0-}$ is selected from the group consisting of F—, Cl—, Br—, or I—.

Specifically, when B is bupivacaine, the structural formula of the conjugate may be:

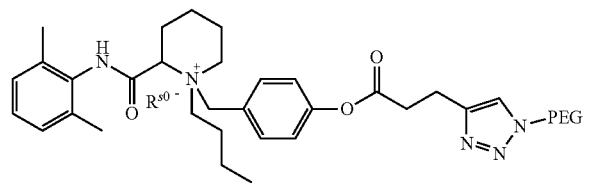

wherein, R$^{s0-}$ is selected from the group consisting of F—, Cl—, Br—, or I—.

Specifically, when B is lidocaine, the structural formula of the conjugate may be:

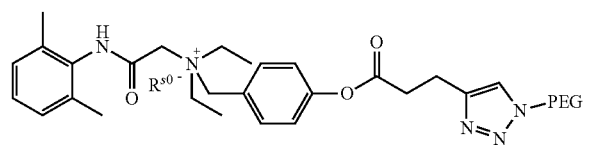

wherein, R$^{s0-}$ is selected from the group consisting of F—, Cl—, Br—, or I—.

In a specific embodiment of the present invention, the conjugate has a structure of the following formula (V):

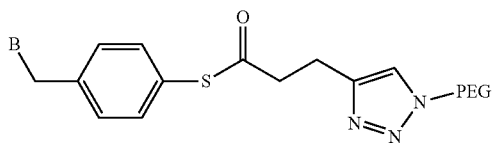
(V)

wherein, a quaternary ammonium salt with a structure of

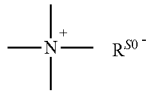

is formed at the linking position between B and —CH$_2$—, and, R$^{s0-}$ is selected from the group consisting of F—, Cl—, Br—, or I—.

Specifically, when B is bupivacaine, the structural formula of the conjugate may be:

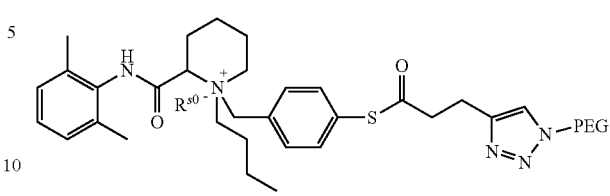

wherein, R$^{s0-}$ is selected from the group consisting of F—, Cl—, Br—, or I—.

In a specific embodiment of the present invention, the conjugate has a structure of the following formula (VI):

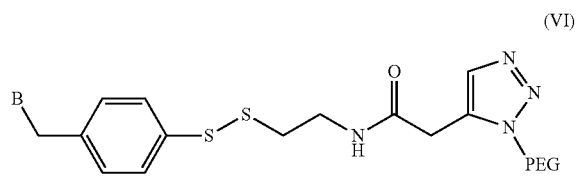
(VI)

wherein, a quaternary ammonium salt with a structure of

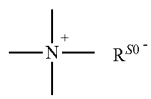

is formed at the linking position between B and —CH$_2$—, and, R$^{s0-}$ is selected from the group consisting of F—, Cl—, Br—, or I—.

Specifically, when B is bupivacaine, the structural formula of the conjugate may be:

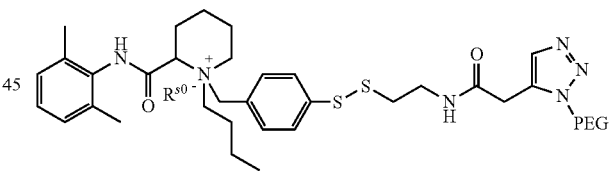

wherein, R$^{s0-}$ is selected from the group consisting of F—, Cl—, Br—, or I—.

In a specific embodiment of the present invention, the conjugate has a structure of the following formula (VII):

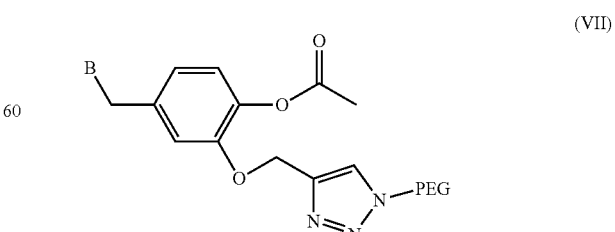
(VII)

wherein, a quaternary ammonium salt with a structure of

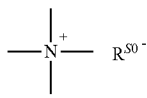

is formed at the linking position between B and —CH$_2$—, and, R$^{s0-}$ is selected from the group consisting of F—, Cl—, Br—, or I—.

Specifically, when B is bupivacaine, the structural formula of the conjugate may be:

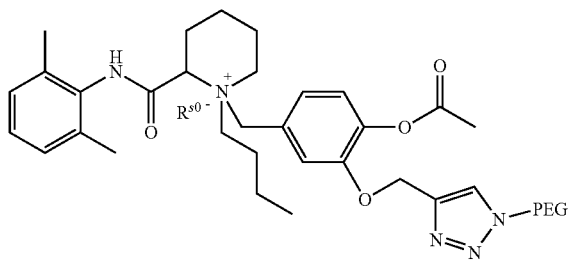

wherein, R$^{s0-}$ is selected from the group consisting of F—, Cl—, Br—, or I—.

In a specific embodiment of the present invention, the conjugate has a structure of the following formula (VIII):

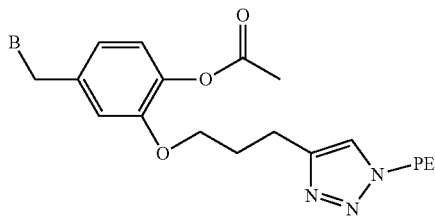

(VIII)

wherein, a quaternary ammonium salt with a structure of

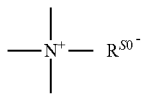

is formed at the linking position between B and —CH$_2$—, and, R$^{s0-}$ is selected from the group consisting of F—, Cl—, Br—, or I—.

Specifically, when B is bupivacaine, the structural formula of the conjugate may be:

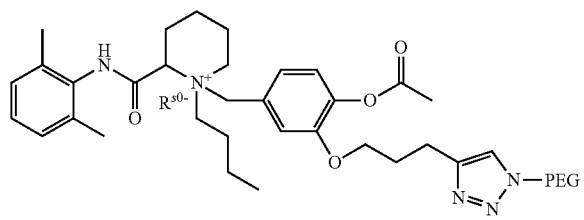

wherein, R$^{s0-}$ is selected from the group consisting of F—, Cl—, Br—, or I—.

In a specific embodiment of the present invention, the conjugate has a structure of the following formula (IX):

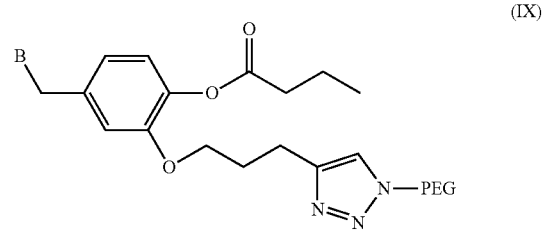

(IX)

wherein, a quaternary ammonium salt with a structure of

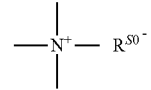

is formed at the linking position between B and —CH$_2$—, and, R$^{s0-}$ is selected from the group consisting of F—, Cl—, Br—, or I—.

Specifically, when B is bupivacaine, the structural formula of the conjugate may be:

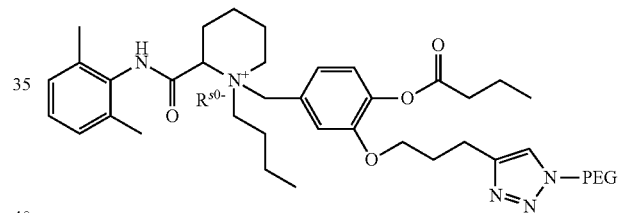

wherein, R$^{s0-}$ is selected from the group consisting of F—, Cl—, Br—, or I—.

In a specific embodiment of the present invention, the conjugate has a structure of the following formula (X):

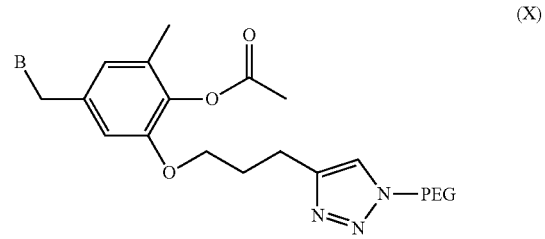

(X)

wherein, a quaternary ammonium salt with a structure of

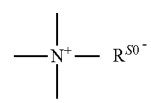

is formed at the linking position between B and —CH$_2$—, and, R$^{s0-}$ is selected from the group consisting of F—, Cl—, Br—, or I—.

Specifically, when B is bupivacaine, the structural formula of the conjugate may be:

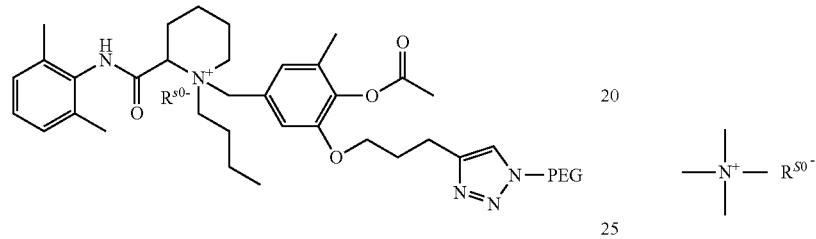

wherein, R$^{s0}$ is selected from the group consisting of F—, Cl—, Br—, or I—.

In a specific embodiment of the present invention, the conjugate has a structure of the following formula (XI):

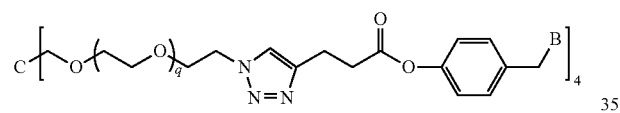

wherein, a quaternary ammonium salt with a structure of

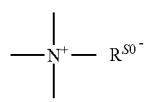

is formed at the linking position between B and —CH$_2$—, and, R$^{s0-}$ is selected from the group consisting of F—, Cl—, Br—, or I—.

In a specific embodiment of the present invention, the conjugate has a structure of the following formula (XII):

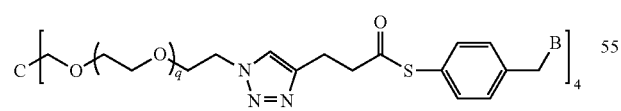

wherein, a quaternary ammonium salt with a structure of

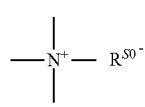

is formed at the linking position between B and —CH$_2$—, and, R$^{s0-}$ is selected from the group consisting of F—, Cl—, Br—, or I—.

In a specific embodiment of the present invention, the conjugate has a structure of the following formula (XIII):

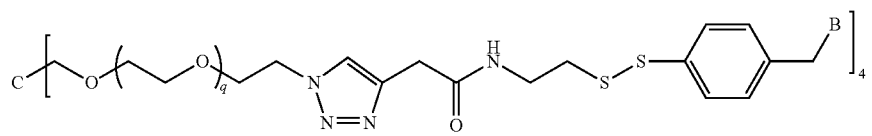

wherein, a quaternary ammonium salt with a structure of

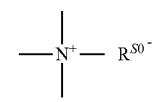

is formed at the linking position between B and —CH$_2$—, and, R$^{s0-}$ is selected from the group consisting of F—, Cl—, Br—, or I—.

In a specific embodiment of the present invention, the conjugate has a structure of the following formula (XIV):

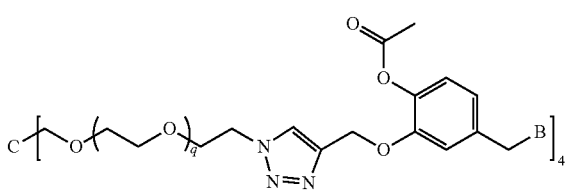

wherein, a quaternary ammonium salt with a structure of

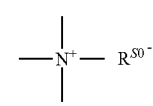

is formed at the linking position between B and —CH$_2$—, and, R$^{s0-}$ is selected from the group consisting of F—, Cl—, Br—, or I—.

In a specific embodiment of the present invention, the conjugate has a structure of the following formula (XV):

(XV)

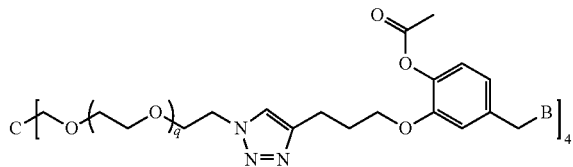

wherein, a quaternary ammonium salt with a structure of

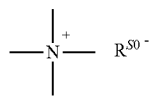

is formed at the linking position between B and —CH$_2$—, and, R$^{s0-}$ is selected from the group consisting of F—, Cl—, Br—, or I—.

In a specific embodiment of the present invention, the conjugate has a structure of the following formula (XVI):

(XVI)

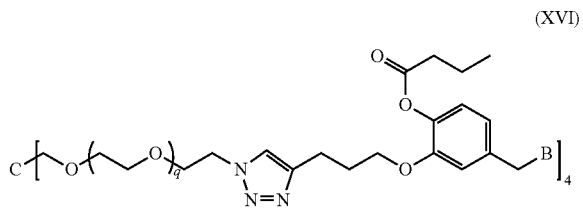

wherein, a quaternary ammonium salt with a structure of

is formed at the linking position between B and —CH$_2$—, and, R$^{s0-}$ is selected from the group consisting of F—, Cl—, Br—, or I—.

In a specific embodiment of the present invention, the conjugate has a structure of the following formula (XVII):

(XVII)

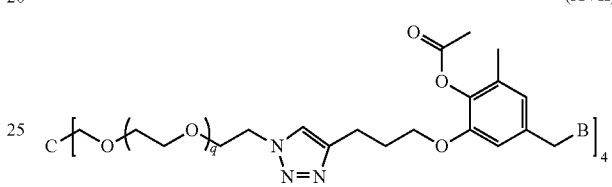

wherein, a quaternary ammonium salt with a structure of

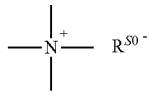

is formed at the linking position between B and —CH$_2$—, and, R$^{s0-}$ is selected from the group consisting of F—, Cl—, Br—, or I—.

In a specific embodiment of the present invention, the conjugate has a structure of the following formula (XVIII):

(XVIII)

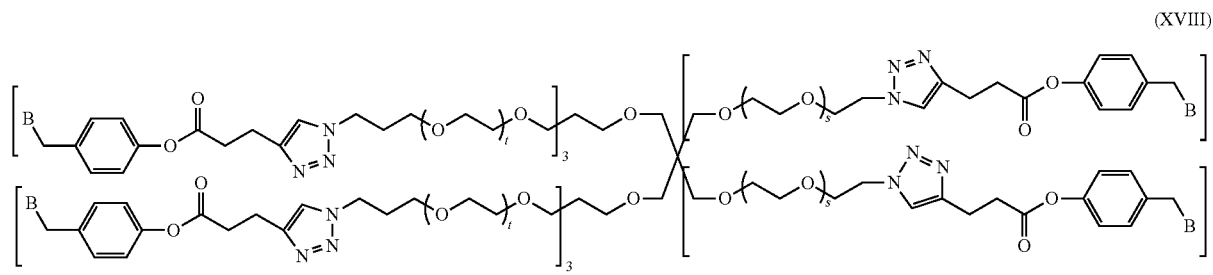

wherein, a quaternary ammonium salt with a structure of

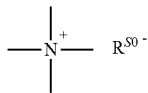

is formed at the linking position between B and —CH$_2$—, and, R$^{s0-}$ is selected from the group consisting of F—, Cl—, Br—, or I—.

In a specific embodiment of the present invention, the conjugate has a structure of the following formula (XIX):

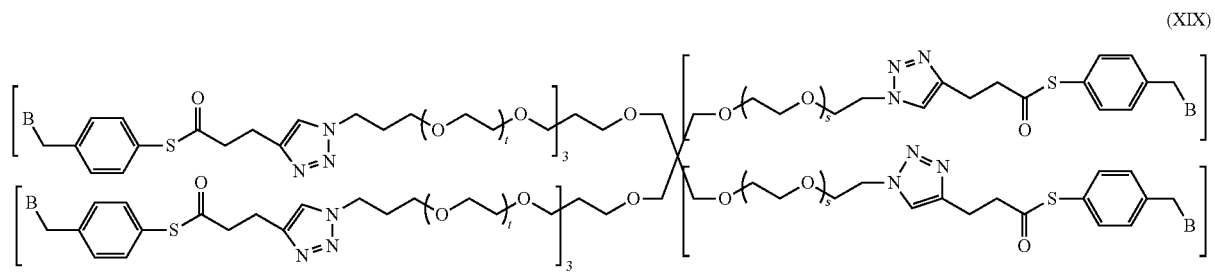

(XIX)

wherein, a quaternary ammonium salt with a structure of

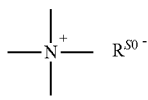

is formed at the linking position between B and —CH$_2$—, and, R$^{s0-}$ is selected from the group consisting of F—, Cl—, Br—, or I—.

In a specific embodiment of the present invention, the conjugate has a structure of the following formula (XX):

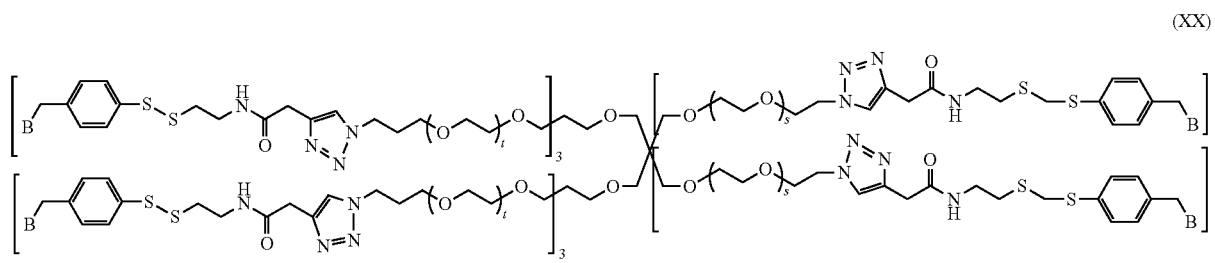

(XX)

wherein, a quaternary ammonium salt with a structure of

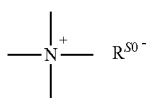

is formed at the linking position between B and —CH$_2$—, and, R$^{s0-}$ is selected from the group consisting of F—, Cl—, Br—, or I—.

In a specific embodiment of the present invention, the conjugate has a structure of the following formula (XXI):

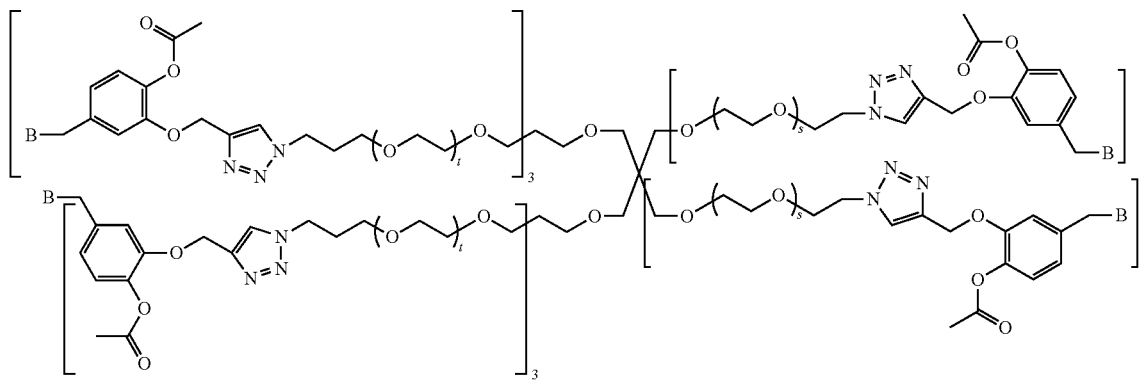

(XXI)

wherein, a quaternary ammonium salt with a structure of

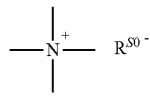

is formed at the linking position between B and —CH$_2$—, and, R$^{s0-}$ is selected from the group consisting of F—, Cl—, Br—, or I—.

In a specific embodiment of the present invention, the conjugate has a structure of the following formula (XXII):

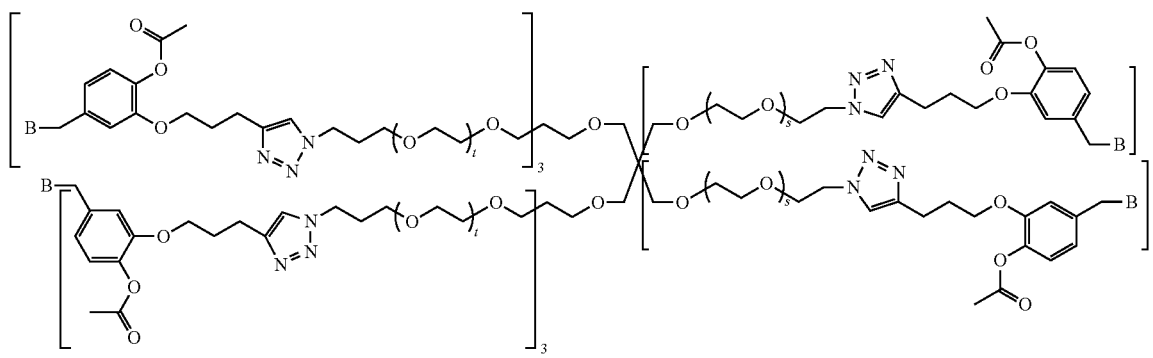

(XXII)

wherein, a quaternary ammonium salt with a structure of

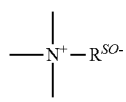

is formed at the linking position between B and —CH$_2$—, and, R$^{s0-}$ is selected from the group consisting of F—, Cl—, Br—, or I—.

In a specific embodiment of the present invention, the conjugate has a structure of the following formula (XXIII):

(XXIII)

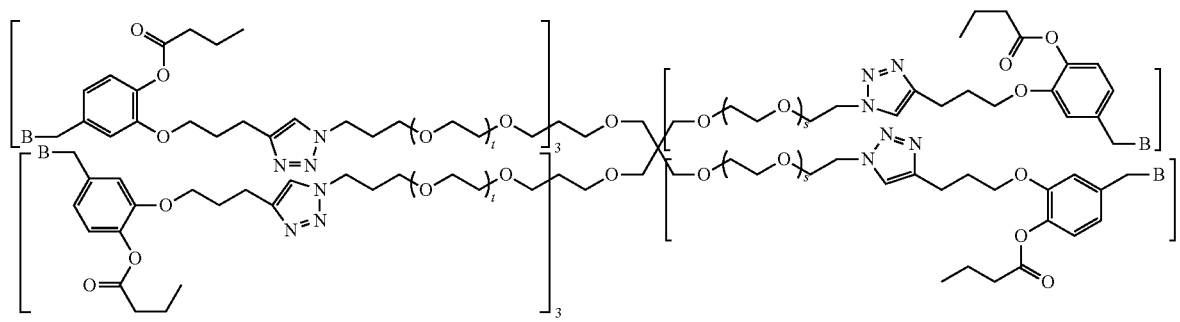

wherein, a quaternary ammonium salt with a structure of

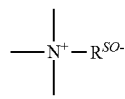

is formed at the linking position between B and —CH$_2$—, and, R$^{s0-}$ is selected from the group consisting of F—, Cl—, Br—, or I—.

In a specific embodiment of the present invention, the conjugate has a structure of the following formula (XXIV):

(XXIV)

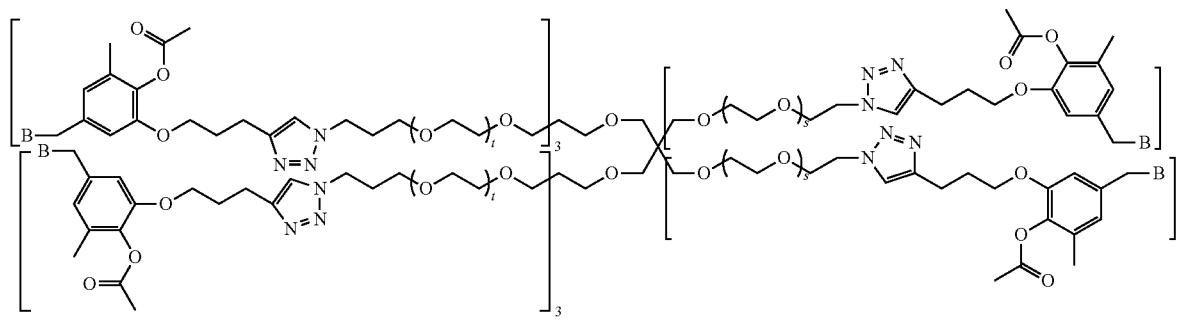

wherein, a quaternary ammonium salt with a structure of

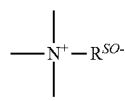

is formed at the linking position between B and —CH$_2$—, and, R$^{s0-}$ is selected from the group consisting of F—, Cl—, Br—, or I—.

In a specific embodiment of the present invention, the conjugate has a structure of the following formula (XXV):

(XXV)

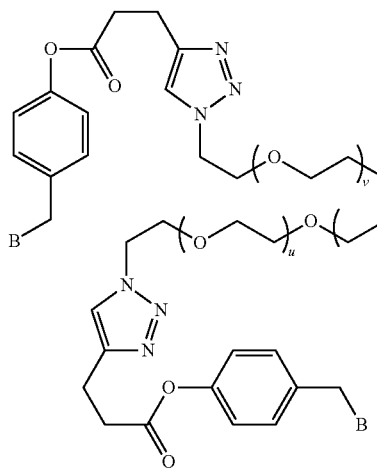 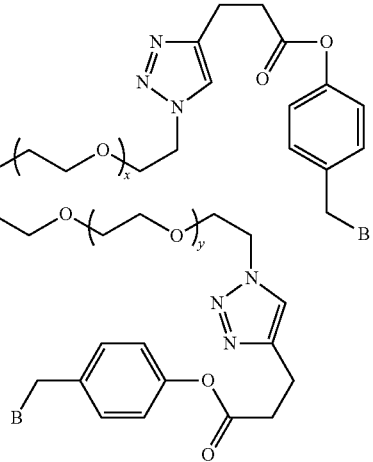

wherein, a quaternary ammonium salt with a structure of

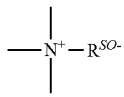

is formed at the linking position between B and —CH$_2$—, and, R$^{s0-}$ is selected from the group consisting of F—, Cl—, Br—, or I—.

In a specific embodiment of the present invention, the conjugate has a structure of the following formula (XXVI):

(XXVI)

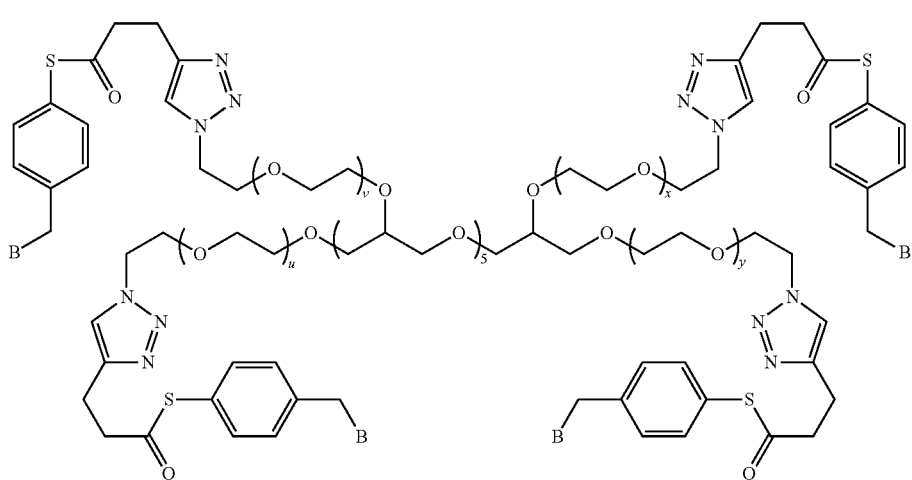

wherein, a quaternary ammonium salt with a structure of

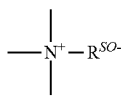

is formed at the linking position between B and —CH$_2$—, and, R$^{s0-}$ is selected from the group consisting of F—, Cl—, Br—, or I—.

In a specific embodiment of the present invention, the conjugate has a structure of the following formula (XXVII):

(XXVII)

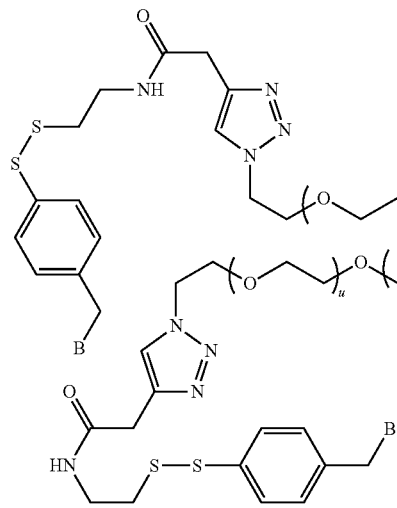
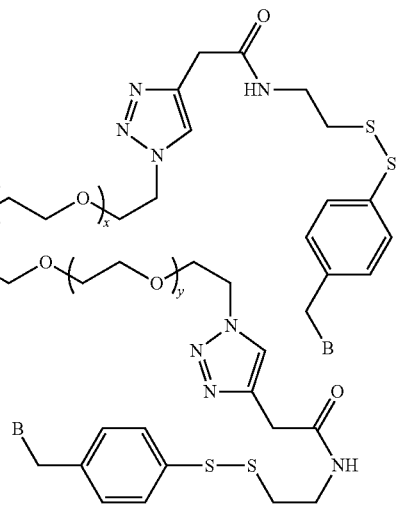

wherein, a quaternary ammonium salt with a structure of

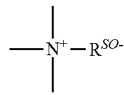

is formed at the linking position between B and —CH$_2$—, and, R$^{so-}$ is selected from the group consisting of F—, Cl—, Br—, or I—.

In a specific embodiment of the present invention, the conjugate has a structure of the following formula (XXVIII):

wherein, a quaternary ammonium salt with a structure of

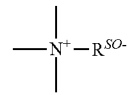

is formed at the linking position between B and —CH$_2$—, and, R$^{so-}$ is selected from the group consisting of F—, Cl—, Br—, or I—.

In a specific embodiment of the present invention, the conjugate has a structure of the following formula (XXIX):

(XXVIII)

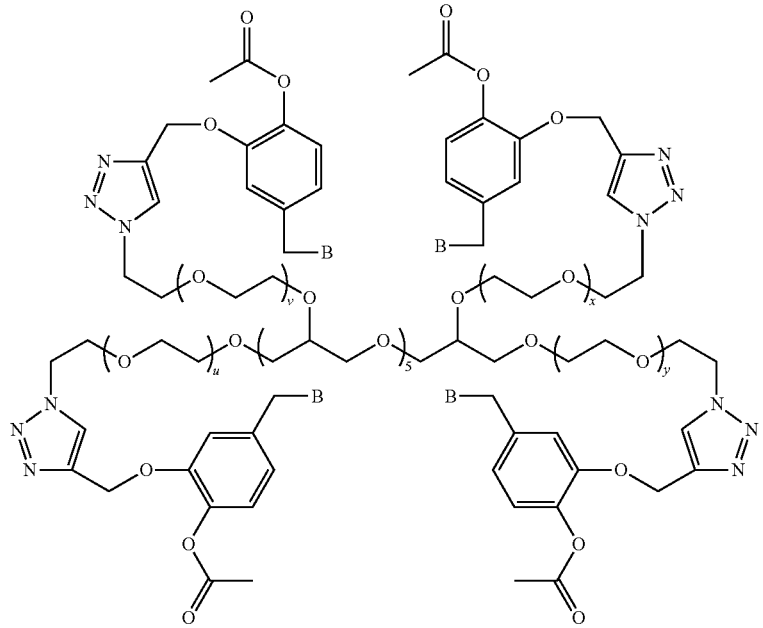

(XXIX)

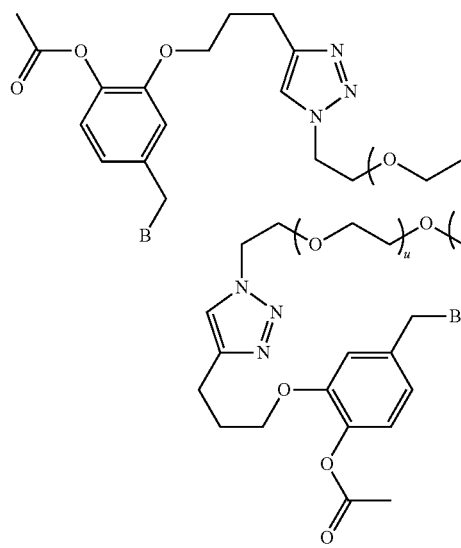
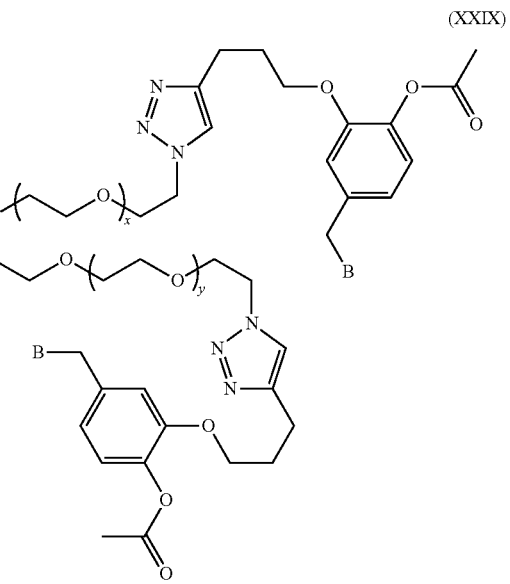

wherein, a quaternary ammonium salt with a structure of

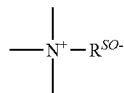

is formed at the linking position between B and —CH$_2$—, and, R$^{s0-}$ is selected from the group consisting of F—, Cl—, Br—, or I—.

In a specific embodiment of the present invention, the conjugate has a structure of the following formula (XXX):

wherein, a quaternary ammonium salt with a structure of

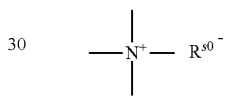

is formed at the linking position between B and —CH$_2$—, and, R$^{s0-}$ is selected from the group consisting of F—, Cl—, Br—, or I—.

In a specific embodiment of the present invention, the conjugate has a structure of the following formula (XXXI):

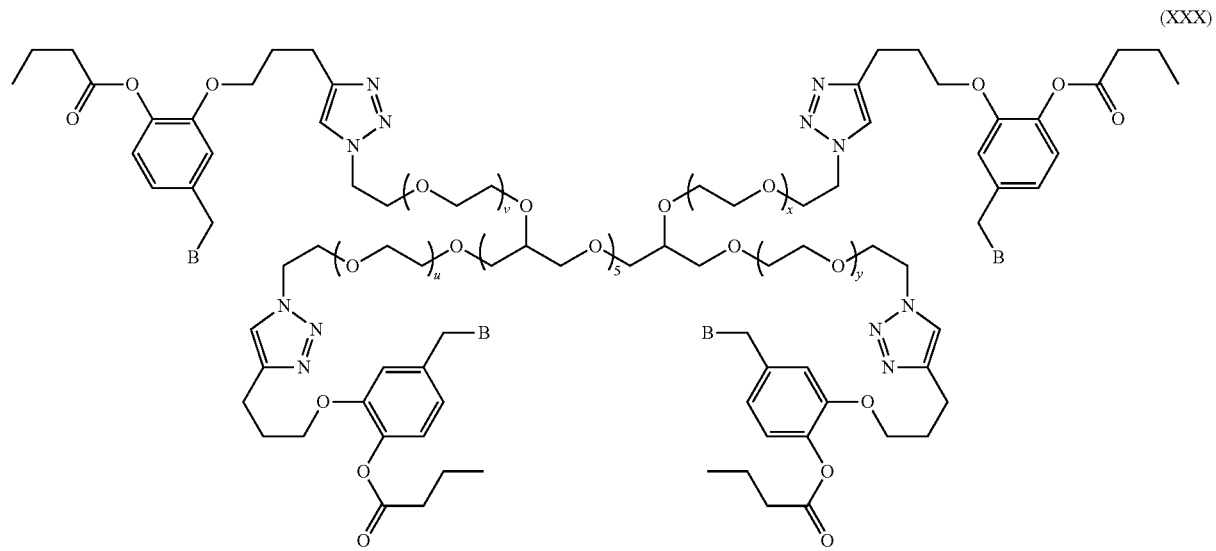

(XXX)

(XXXI)

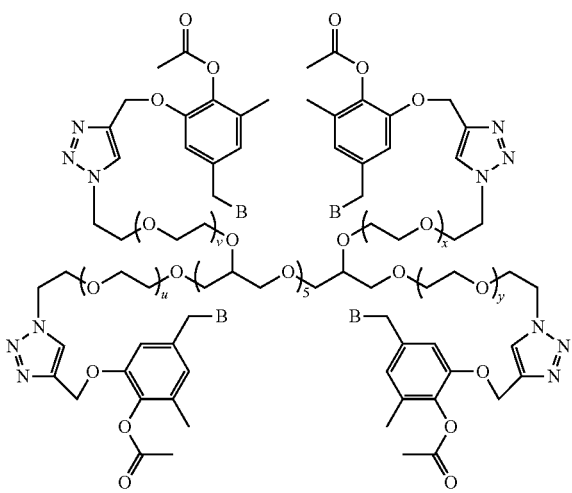

wherein, a quaternary ammonium salt with a structure of

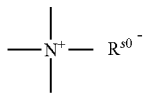

is formed at the linking position between B and —CH$_2$—, and, R$^{s0-}$ is selected from the group consisting of F—, Cl—, Br—, or I—.

The present invention also provides a pharmaceutical composition comprising the conjugate of the present invention and a pharmaceutically acceptable carrier or excipient.

In some embodiments, according to the required drug-delivery way, the pharmaceutically acceptable composition may comprise from about 1 to about 99% by weight of the conjugate of the present invention, and from 99 to 1% by weight of a suitable carrier or pharmaceutically acceptable excipient. Preferably, the composition comprises from about 5 to 75% by weight of the conjugate of the present invention, and the balance of a suitable carrier or pharmaceutically acceptable excipient. More preferably, the composition comprises about 10 to 50% by weight of the conjugate of the present invention and the balance of a suitable carrier or pharmaceutically acceptable excipient.

In some embodiments, the pharmaceutical composition of the present invention may also comprise minor amount of auxiliary substances such as wetting or emulsifying agents, pH buffer, antioxidant and the like, e.g., citric acid, sorbitan monolaurate, triethanolamine oleate, butylated hydroxytoluene and the like.

In some embodiments, the pharmaceutical composition is in the form of a tablet, capsule, pill, granule, powder, suppository, injection, solution, suspension, paste, patch, lotion, drop, liniment, spray or other dosage forms.

In some embodiments, the conjugate of the present invention may be administered in the form of a pure compound or a suitable pharmaceutical composition and may be administered by any acceptable drug-delivery way or as a reagent for a similar purpose. Thus, the drug-delivery way employed may be selected by oral, intranasal, parenteral, topical, transdermal or rectal, in the form of solid, semi-solid or liquid pharmaceuticals, e.g., tablets, suppositories, pills, soft and hard gelatin capsules, powders, solutions, suspensions and injections, preferably in a unit dosage form suitable for simple administration of a precise dose.

A pharmaceutical composition in the form of a liquid may be adopted, e.g., the conjugate of the present invention (about 0.5 to about 20%) and pharmaceutically acceptable adjuvant selectively present may be dissolved or dispersed in a carrier by dissolving, dispersing and other means, the examples of the carrier being water, saline, glucose hydrate, glycerol, ethanol and the like, so as to form a solution or a suspension.

The present invention also provides, in one aspect, an application of the conjugate and pharmaceutical composition thereof of the present invention for the manufacture of a medicament for analgesic or the treatment of chronic pain.

In addition, the present invention further provides a preparation method of the conjugate of the present invention comprising the following steps: (1) obtaining a linking group with one end group of alkynyl or azido at one end and one halogenated or sulfonated end group at one end with a structure represented by the following formula M$_1$ or M$_2$; (2) reacting the linking group obtained in step (1) with an anesthetic to form a quaternary ammonium salt; (3) reacting the alkynyl or azido of the quaternary ammonium salt obtained in step (2) with PEG modified with end group modified by azido or alkynyl to form the structure;

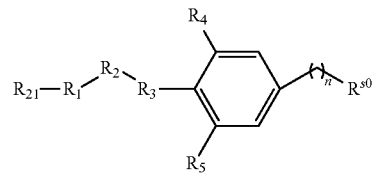

(M$_1$)

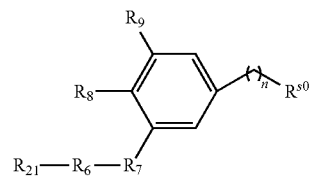

(M$_2$)

wherein:

PEG is a polyethylene glycol residue with a molecular weight of 1-100 KDa;

n is an integer of 1-6, preferably 1, 2 or 3;

R$_{21}$ is selected from alkynyl or azido;

R$^{s0-}$ is selected from the group consisting of F—, Cl—, Br—, I—, methanesulfonate, ethanesulfonate, benzenesulfonate, citrate, lactate, succinate, fumarate, glutamate, citrate, salicylate, and maleate, preferably, R$^{s0-}$ is selected from the group consisting of F—, Cl—, Br—, I—, methanesulfonate, ethanesulfonate, and benzenesulfonate;

wherein, R$_1$ and R$_6$ are independently selected from C$_{1-6}$ alkyl, preferably methyl, ethyl, propyl, or R$_1$ and R$_6$ are independently selected from —(CH$_2$)iNHCO(CH$_2$)j-, and —(CH$_2$)iCONH(CH$_2$)j-, i and j are integer independently selected from 0 to 6, preferably 1, 2, or 3;

R$_2$ is selected from the group consisting of —C=O, —C=S, —O— or —S—;

R$_3$ and R$_7$ are independently selected from the group consisting of —O— or —S—;

R$_4$ or R$_5$ is independently selected from the group consisting of H, C$_{1-6}$ alkyl or halogen, preferably H, methyl or ethyl;

$R_8$ or $R_9$ is independently selected from the group consisting of H, $C_{1-6}$ alkyl or —O(C═O)($CH_2$)$iCH_3$, i is an integer of 0-6, preferably H, methyl, ethyl, propyl, acetoxy, propionyloxy, or butyryloxy;

and, the H atom of the alkynyl end group may be substituted with $R_{s1}$, $R_{s1}$ is selected from the group consisting of H or $C_{1-6}$ alkyl, preferably H, methyl, ethyl or propyl.

In some embodiments, the linking group in step (1) is selected from the group consisting of the structures shown in $M_3$-$M_6$ below:

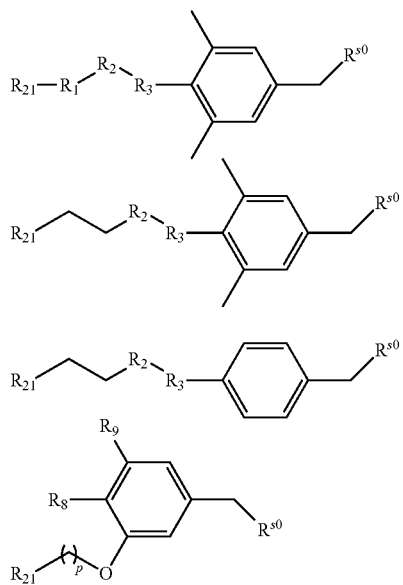

wherein:

$R_{21}$ is selected from the group consisting of alkynyl or azido;

$R^{s0-}$ is selected from the group consisting of F—, Cl—, Br—, and I—;

$R_1$ is methyl, ethyl, propyl or —($CH_2$)iNHCO($CH_2$)j-, —($CH_2$)iCONH($CH_2$)j-, i and j are independently selected from 1, 2 or 3;

$R_2$ is —C═O, —O— or —S—;

$R_3$ is —O— or —S—;

$R_8$ is acetoxy, propionyloxy or butyryloxy;

$R_9$ is H or methyl;

and, P is 1, 2 or 3.

In the present invention, the anesthetic contains a tertiary amine structure, forms a quaternary ammonium salt through the linking group and is introduced with polyethylene glycol, which can achieve the goal of prolonging the duration of anesthetics to achieve sustained release and controlled release, in addition, the drug has a high stability, and can effectively play the role of analgesia.

DETAILED DESCRIPTION OF THE INVENTION

The following examples are provided to illustrate the present invention, but are not intended to limit the present invention.

The polyethylene glycol used in the examples is provided by Beijing JenKem Technology Co., Ltd., unless specified, the molecular weight is 20K. Other reagents are commercially available.

Example 1 Synthesis of Linking Chain (L1)

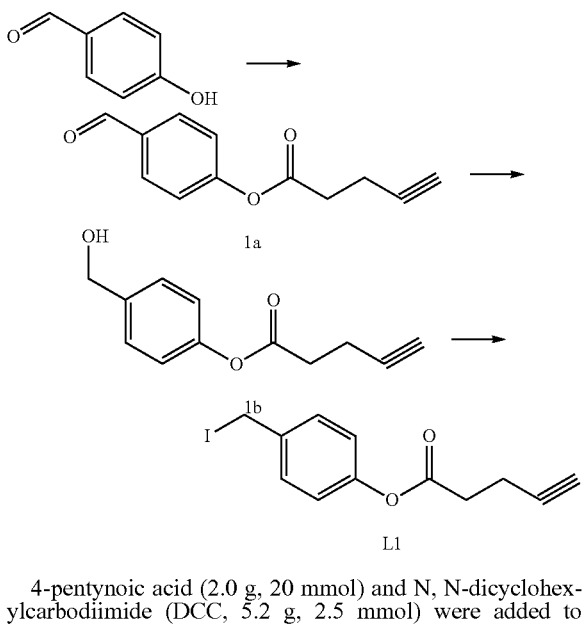

4-pentynoic acid (2.0 g, 20 mmol) and N, N-dicyclohexylcarbodiimide (DCC, 5.2 g, 2.5 mmol) were added to dichloromethane (50 mL), cooled in an ice-water bath, then p-hydroxybenzaldehyde (2.68 g, 22 mmol) was added, the ice-water bath was removed after completion of addition, and the resulting mixture was reacted at room temperature overnight, and filtered, the filter cake was washed with ethyl acetate and the filtrate was evaporated to dryness to obtain a crude product, which was purified by column chromatography to give 3.5 g of product 1a.

The compound 1a (3.23 g, 16 mmol) was added to anhydrous methanol (35 mL), cooled to 0° C., then sodium borohydride (365 mg, 9.6 mmol) was added, the reaction was carried out at the same temperature for 10 min and then quenched with 1 M HCl, the resulting mixture was subjected to rotary evaporation to remove methanol, and further added with ethyl acetate and saturated brine, the aqueous phase was extracted with ethyl acetate, and the organic phases were combined, washed with saturated brine, dried, filtered and concentrated to give a crude product, which was purified by column chromatography to give 1.8 g of product 1b.

Iodine (3.35 g, 13.2 mmol), triphenylphosphine (3.46 g, 13.2 mmol) and imidazole (0.9 g, 13.2 mmol) were added to dichloromethane (30 mL), stirred at 0° C. for 20 min, a solution of product 1b (1.8 g, 8.8 mmol) in dichloromethane (7.5 mL) was added, and the resulting mixture was reacted at 0° C. for 30 min, and then washed with 2N hydrochloric acid, saturated sodium bisulfite solution and brine, respectively, dried and evaporated to dryness to obtain a crude product, which was purified by column chromatography to give 2.4 g of product L1. 1H NMR: (CDCl3): 2.03 (s, 1H), 2.61 (t, 2H), 2.77 (t, 2H), 4.44 (s, 2H), 7.01 (d, 2H), 7.39 (d, 2H).

Example 2 Synthesis of Quaternary Ammonium Salt of Lidocaine (Y1)

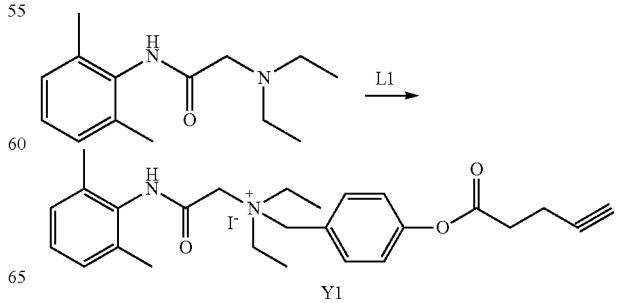

Lidocaine (0.50 g, 2.13 mmol) and compound L1 (1.0 g, 3.19 mmol) were added to acetonitrile (20 mL) and reacted at 50° C. overnight. TLC monitoring showed that the lidocaine was reacted completely, and the reaction liquid was concentrated to give a crude product, which was purified by column chromatography to give 1.2 g of product Y1. 1H-NMR: (CDCl3): 1.59 (m, 6H), 2.06 (s, 2H), 2.31 (s, 6H), 2.64 (m, 2H), 2.87 (m, 2H), 3.49 (m, 2H), 3.71 (m, 2H), 4.89 (s, 2H), 4.93 (s, 2H), 7.06 (m, 3H), 7.28 (d, 2H), 7.62 (d, 2H), 9.79 (s, 1H).

Example 3 Synthesis of Conjugate 1 of Lidocaine (mPEG-Lidocaine, 20 K)

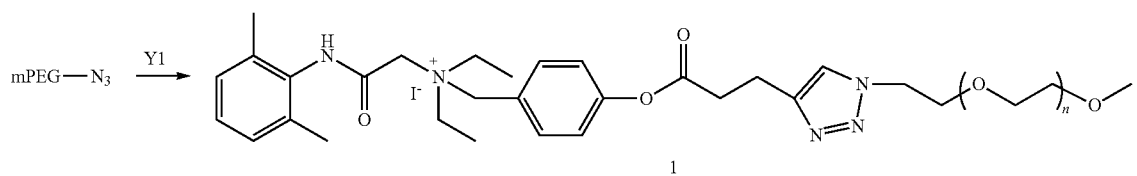

mPEG-N3 (20 K, 2 g, 0.1 mmol), compound Y1 (65.8 mg, 0.12 mmol), vitamin C (52.8 mg, 3 mmol) were added to N,N-dimethylformamide (20 mL), the resulting mixture was rapidly stirred to dissolve, then added with an aqueous solution (4.4 mL, 2.2 mL/g PEG) of copper sulfate pentahydrate (30 mg, 0.12 mmol), the resulting mixture was reacted at room temperature overnight and precipitated with isopropanol to give 1.9 g of product. 1H NMR: (CDCl3): 1.42 (m, 6H), 2.19 (s, 6H), 3.02 (m, 4H), 3.23 (m, 4H), 3.31 (s, 3H), 3.50 (m, 1800H), 3.80 (m, 2H) (m, 2H), 4.20 (m, 2H), 4.50 (s, 2H), 4.82 (s, 2H), 7.12 (m, 3H), 7.30 (d, 2H), 7.64 (d, 2H) s, 1H), 10.28 (s, 1H).

Example 4 Synthesis of Conjugate 2 of Lidocaine (4-Arm-PEG-Lidocaine, 10 K)

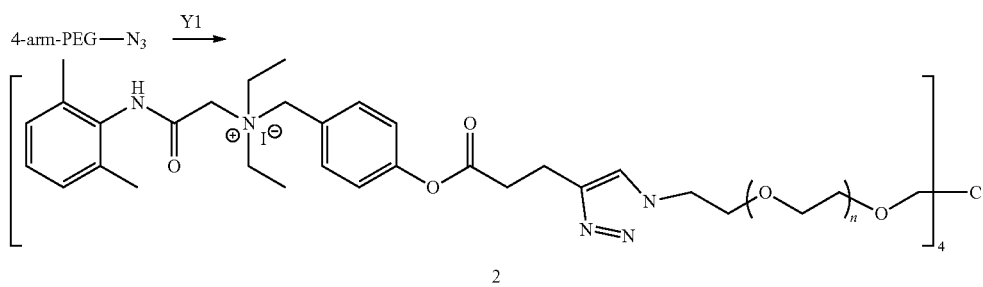

4-arm-PEG-N3 (10 K, 2 g, 0.2 mmol), compound Y1 (548.5 mg, 1 mmol), vitamin C (440 mg, 2.5 mmol) were added to N, N-dimethylformamide (20 mL), the resulting mixture was rapidly stirred to dissolve, then added with an aqueous solution (4.4 mL, 2.2 mL/g PEG) of copper sulfate pentahydrate (250 mg, 1 mmol), the resulting mixture was reacted at room temperature overnight and precipitated with isopropanol to give 1.8 g of product. 1H NMR: (CDCl3): 1.43 (m, 24H), 2.22 (s, 24H), 3.07 (m, 16H), 3.25 (m, 16H), 3.34 (s, 12H), 3.50 (m, 900H), 3.83 (m, 8H), 4.22 (m, 8H), 4.53 (s, 8H), 4.85 (s, 8H), 7.13 (m, 12H), 7.30 (d, 8H), 7.65 (d, 8H), 7.92 (s, 4H), 10.26 (s, 4H).

Example 5 Synthesis of Conjugate 3 of Lidocaine (8-Arm-PEG-Lidocaine, 20 K)

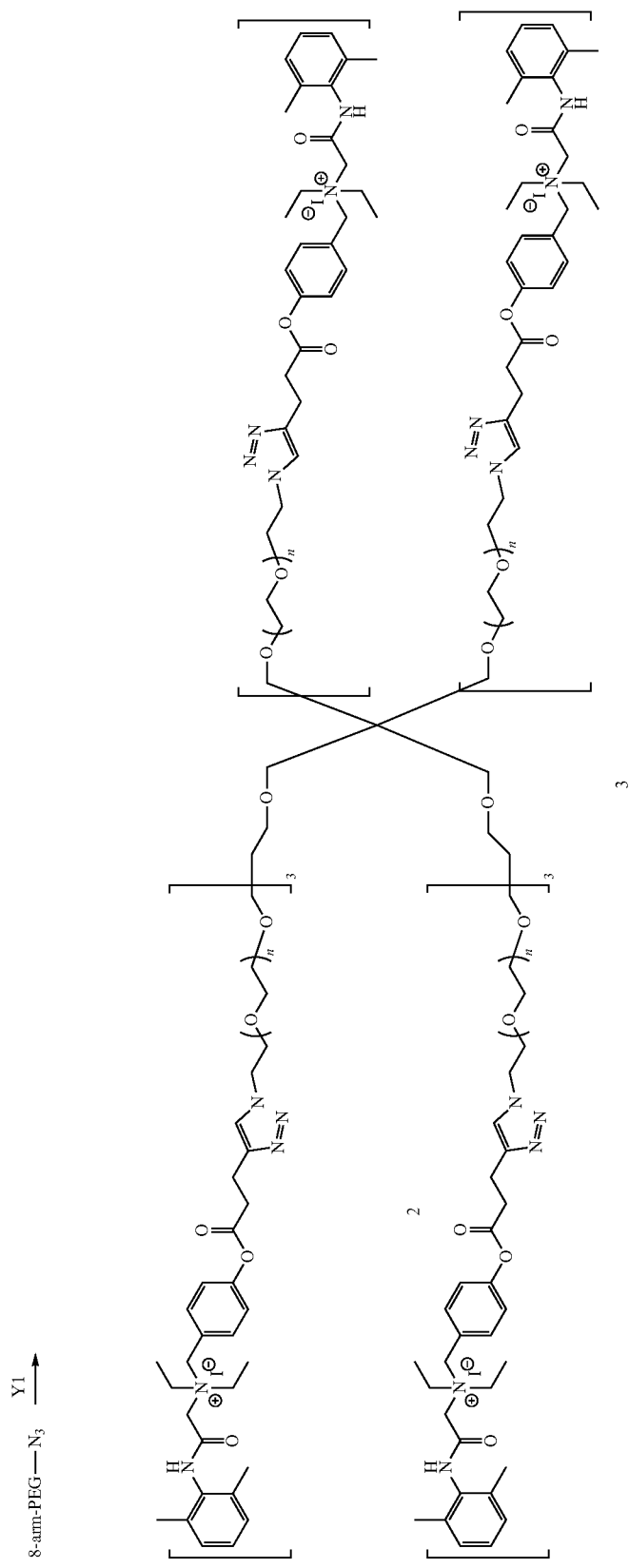

8-arm-PEG-N3 (20 K, 2 g, 0.1 mmol), compound Y1 (548.5 mg, 1 mmol), vitamin C (440 mg, 2.5 mmol) were added to N, N-dimethylformamide (20 mL), the resulting mixture was rapidly stirred to dissolve, then added with an aqueous solution (4.4 mL, 2.2 mL/g PEG) of copper sulfate pentahydrate (250 mg, 1 mmol), the resulting mixture was reacted at room temperature overnight and precipitated with isopropanol to give 1.6 g of product. 1H NMR: (CDCl3): 1.44 (M, 48H), 2.22 (s, 48H), 3.09 (m, 32H), 3.23 (m, 32H), 3.37 (s, 24H), 3.51 (m, 1800H), 3.84 (m, 16H) (m, 16H), 4.23 (m, 16H), 4.54 (s, 16H), 4.86 (s, 16H), 7.12 (m, 24H), 7.31 (d, 16H), 7.66 (d, 16H), 7.93 (s, 8H), 10.27 (s, 8H).

Example 6 Synthesis of Quaternary Ammonium Salt of Bupivacaine (Y2)

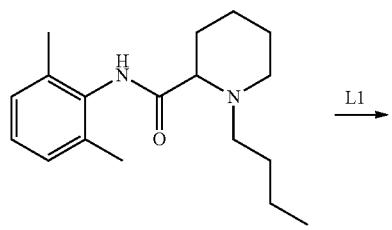

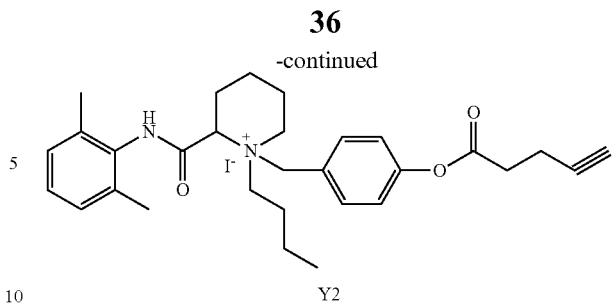

Bupivacaine (0.50 g, 1.74 mmol) and compound L1 (1.0 g, 3.19 mmol) were added to acetonitrile (20 mL) and reacted at 50° C. overnight. TLC monitoring showed that the bupivacaine was reacted completely, and the reaction liquid was concentrated to give a crude product, which was purified by column chromatography to give 1.1 g of product Y2. 1H NMR: (CDCl3): 1.09 (m, 3H), 1.46 (m, 3H), 1.85 (m, 4H), 2.19 (m, 1H), 2.30 (s, 6H), 2.61 (m, 2H), 2.76 (m, 2H), 2.93 (s, 1H), 3.30 (m, 2H), 3.39 (m, 2H), 3.71 (m, 2H), 4.91 (s, 2H), 4.96 (s, 2H), 7.18 (m, 3H), 7.26 (d, 2H), 7.42 (d, 2H), 10.15 (s, 1H).

Example 7 Synthesis of Conjugate 4 of Bupivacaine (mPEG-Bupivacaine, 20 K)

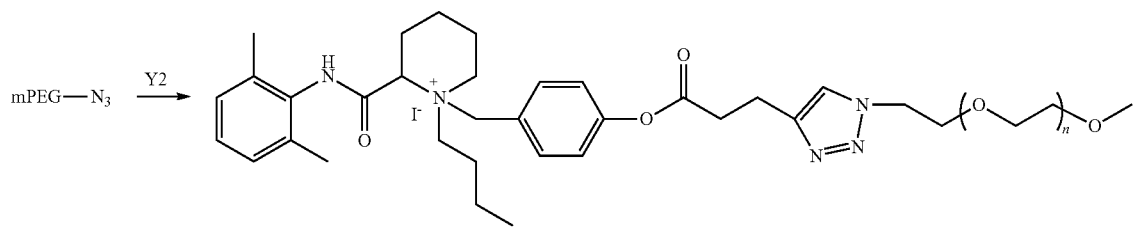

mPEG-N3 (20 K, 2 g, 0.1 mmol), compound Y2 (89.7 mg, 0.12 mmol), vitamin C (52.8 mg, 3 mmol) were added to N, N-dimethylformamide (20 mL), the resulting mixture was rapidly stirred to dissolve, then added with an aqueous solution (4.4 mL, 2.2 mL/g PEG) of copper sulfate pentahydrate (30 mg, 0.12 mmol), the resulting mixture was reacted at room temperature overnight and precipitated with isopropanol to give 1.7 g of product. 1H NMR: (CDCl3): 1.09 (m, 3H), 1.25 (m, 1H), 1.37 (m, 3H), 1.75 (m, 4H), 1.97 (m, 1H), 2.16 (s, 6H), 2.23 (m, 1H), 2.57 (m, 2H), 2.85 (m, 2H), 3.27 (m, 4H), 3.32 (s, 3H), 3.56 (m, 1800H), 3.95 (m, 2H), 4.10 (m, 2H), 4.52 (s, 2H), 4.60 (s, 2H), 7.19 (m, 3H), 7.27 (d, 2H), 7.30 (d, 2H), 7.69 (s, 1H), 10.19 (s, 1H).

Example 8 Synthesis of Conjugate 5 of Bupivacaine (4-Arm-PEG-Bupivacaine, 10 K)

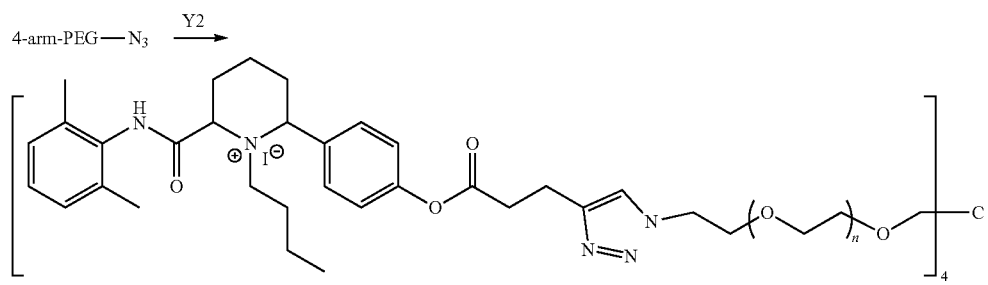

4-arm-PEG-N3 (10 K, 2 g, 0.2 mmol), compound Y2 (747.7 mg, 1 mmol), vitamin C (440 mg, 2.5 mmol) were added to N, N-dimethylformamide (20 mL), the resulting mixture was rapidly stirred to dissolve, then added with an aqueous solution (4.4 mL, 2.2 mL/g PEG) of copper sulfate pentahydrate (250 mg, 1 mmol), the resulting mixture was reacted at room temperature overnight and precipitated with isopropanol to give 1.8 g of product. 1H NMR: (CDCl3): 1.08 (m, 12H), 1.26 (m, 4H), 1.38 (m, 12H), 1.74 (m, 8H), 1.98 (m, 4H), 2.17 (s, 24H), 2.25 (m, 4H), 2.56 (m, 8H), 2.83 (m, 8H), 3.27 (m, 16H), 3.31 (s, 12H), 3.54 (m, 900H), 3.95 (m, 8H), 4.07 (m, 8H), 4.50 (s, 8H), 4.58 (s, 8H), 7.21 (m, 12H), 7.29 (d, 8H), 7.33 (d, 8H), 7.65 (s, 4H), 10.15 (s, 4H).

Example 9 Synthesis of Conjugate 6 of Bupivacaine (8-Arm-PEG-Bupivacaine, 20K)

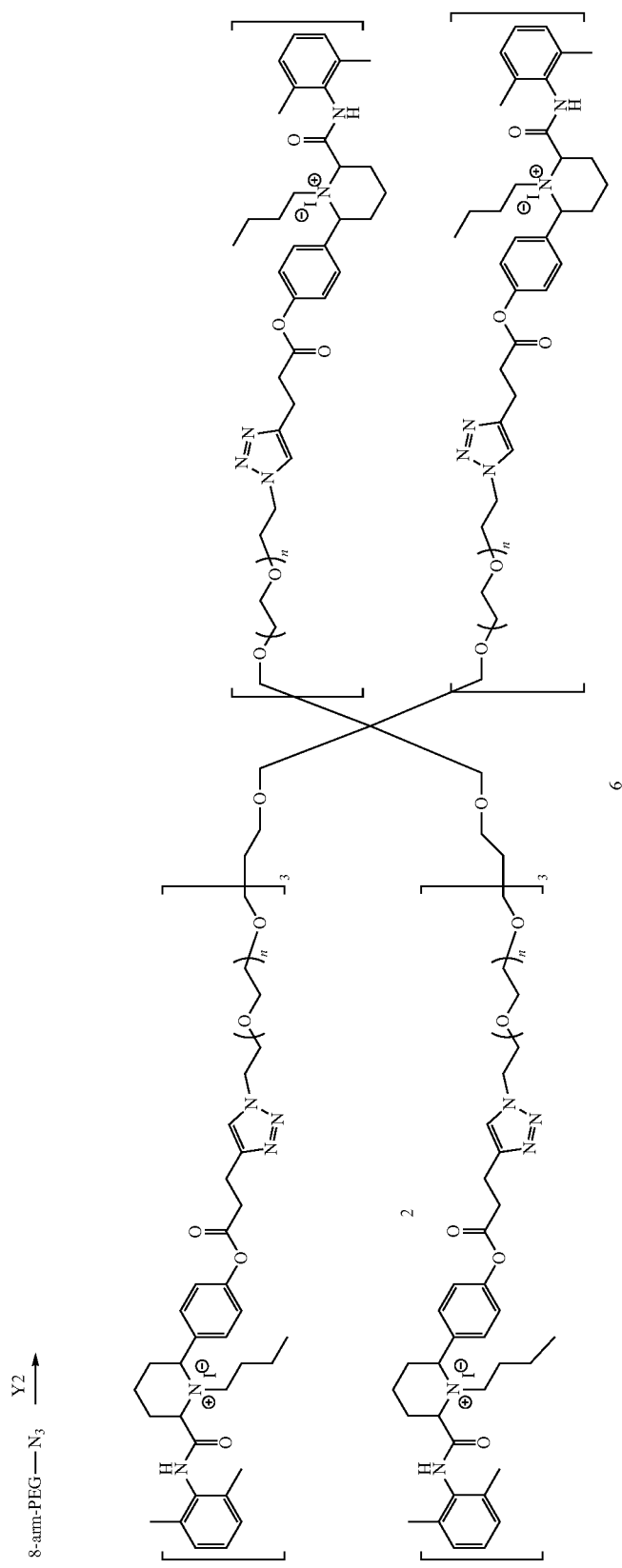

8-arm-PEG-N3 (20 K, 2 g, 0.1 mmol), compound Y2 (747.7 mg, 1 mmol), vitamin C (440 mg, 2.5 mmol) were added to N, N-dimethylformamide (20 mL), the resulting mixture was rapidly stirred to dissolve, then added with an aqueous solution (4.4 mL, 2.2 mL/g PEG) of copper sulfate pentahydrate (250 mg, 1 mmol), the resulting mixture was reacted at room temperature overnight and precipitated with isopropanol to give 1.6 g of product. 1H NMR: (CDCl3): 1H NMR: (CDCl3): 1.09 (m, 24H), 1.26 (m, 8H), 1.39 (m, 24H), 1.73 (m, 16H), 1.97 (m, 8H), 2.17 (s, 48H), 2.24 (m, 8H), 2.57 (m, 16H), 2.81 (m, 16H), 3.27 (m, 32H), 3.32 (s, 24H), 3.51 (m, 1800H), 3.93 (m, 16H), 4.09 (m, 16H), 4.51 (s, 16H), 4.57 (s, 16H), 7.20 (m, 24H), 7.27 (d, 16H), 7.32 (d, 16H), 7.63 (s, 8H), 10.16 (s, 8H).

Example 10 Synthesis of Linking Chain (L2)

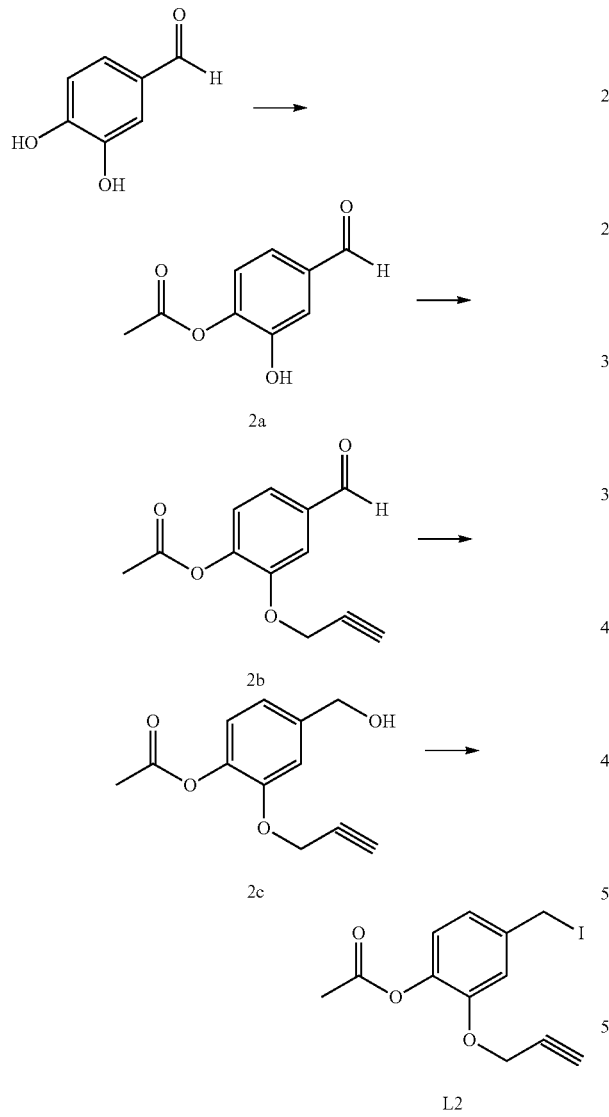

3,4-dihydroxybenzaldehyde (25 g, 181 mmol) was added to N, N-dimethylformamide (180 mL), cooled to 0° C., sodium hydride (7.2 g, 181 mmol) was added in batches, after completion of addition, the resulting mixture was reacted for 10 minutes, then heated to room temperature, acetic anhydride (18.7 g, 183 mmol) was added, and after completion of addition, the resulting mixture was reacted for 4 hours. Ice water and 10% hydrochloric acid were added to the reaction liquid, and the resulting mixture was extracted with ethyl acetate, the organic phases were combined, washed with saturated sodium bicarbonate solution, water and saturated brine, respectively, and dried. The resulting solution was concentrated, and then the resulting residue was crystallized with chloroform to give 19.8 g of product 2a.

3-hydroxy-4-acetoxybenzaldehyde (3.7 g, 30 mmol) and sodium carbonate (12.4 g, 90 mmol) were added to N, N-dimethylformamide (50 mL), the resulting mixture was heated to 60° C. and reacted for half of an hour and then cooled to room temperature, a solution of propargyl bromide in toluene (80%, 4.1 mL) was added, after the completion of addition, the resulting mixture was continued to react at the same temperature, after completion of the reaction, the mixture was poured into ice water and the resulting solution was extracted with diethyl ether, the organic phases were combined, washed with water, dried and concentrated to give 5.3 g of product 2b.

The compound 2b (4.4 g, 20 mmol) was added to anhydrous methanol (50 mL), and cooled to 0° C., then sodium borohydride (456 mg, 12 mmol) was added, the reaction was carried out at the same temperature for 10 min and then quenched with 1 M HCl, the resulting mixture was subjected to rotary evaporation to remove methanol, and further added with ethyl acetate and saturated brine, the aqueous phase was extracted with ethyl acetate, and the organic phases were combined, washed with saturated brine, dried, filtered and concentrated to give a crude product, which was purified by column chromatography to give 3.3 g of product 2c.

Iodine (3.8 g, 15 mmol), triphenylphosphine (3.9 g, 15 mmol) and imidazole (1.0 g, 15 mmol) were added to dichloromethane (30 mL) and stirred at 0° C. for 20 min, a solution of product 2c (2.2 g, 10 mmol) in dichloromethane (10 mL) was added, the resulting mixture was reacted at 0° C. for 30 min, and then washed with 2N hydrochloric acid, saturated sodium bisulfite solution and brine, respectively, dried and evaporated to dryness to obtain a crude product, which was purified by column chromatography to give 2.4 g of product L2. 1H NMR: (CDCl3): 2.35 (s, 3H), 3.37 (s, 1H), 4.51 (s, 2H), 4.72 (s, 2H), 6.77 (d, 1H), 7.02 (s, 1H), 7.09 (d, 1H).

Example 11 Synthesis of Quaternary Ammonium Salt of Lidocaine (Y3)

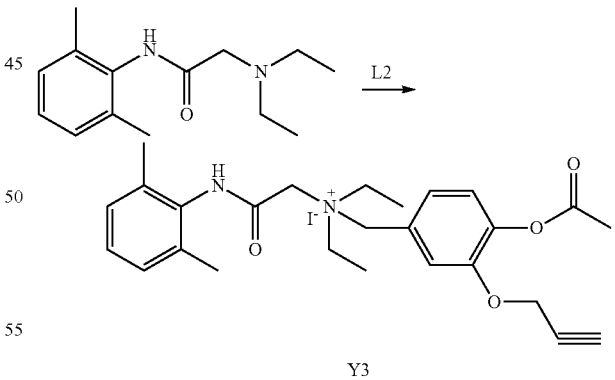

Lidocaine (0.5 g, 2.1 mmol) and compound L2 (1.8 g, 3.2 mmol) were added to acetonitrile (20 mL), and reacted at 50° C. overnight. TLC monitoring showed that the lidocaine was reacted completely, and the reaction liquid was concentrated to give a crude product, which was purified by column chromatography to give 1.4 g of product Y3. 1H NMR: (CDCl3): 1.05 (m, 6H), 2.13 (s, 2H), 2.30 (s, 3H), 2.42 (m, 4H), 3.31 (s, 2H), 3.35 (s, 1H), 3.63 (m, 2H), 4.71 (s, 2H), 6.92 (d, 1H), 7.08 (d, 1H), 7.12 (s, 1H), 7.19 (m, 3H), 9.82 (s, 1H).

Example 12 Synthesis of Conjugate 7 of Lidocaine (4-Arm-PEG-Lidocaine, 10K)

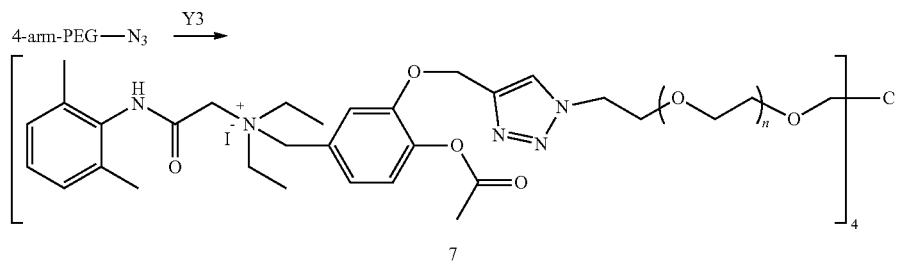

4-arm-PEG-N3 (10 K, 2 g, 0.2 mmol), compound Y3 (564.5 mg, 1 mmol), vitamin C (440 mg, 2.5 mmol) were added to N, N-dimethylformamide (20 mL), the resulting mixture was rapidly stirred to dissolve, then added with an aqueous solution (4.4 mL, 2.2 mL/g PEG) of copper sulfate pentahydrate (250 mg, 1 mmol), the resulting mixture was reacted at room temperature overnight and precipitated with isopropanol to give 1.8 g of product. 1H NMR: (CDCl3): 1.05 (m, 24H), 2.13 (s, 24H), 2.30 (s, 12H), 2.42 (m, 16H), 3.50 (s, 8H), 3.53 (m, 900H), 3.86 (m, 8H), 3.91 (m, 8H), 4.55 (s, 8H), 4.81 (s, 8H), 5.23 (s, 8H), 6.91 (d, 4H), 7.06 (s, 4H), 7.20 (m, 12H), 7.68 (s, 4H), 10.26 (s, 4H).

Example 13 Synthesis of Conjugate 8 of Lidocaine (8-Arm-PEG-Lidocaine, 20K)

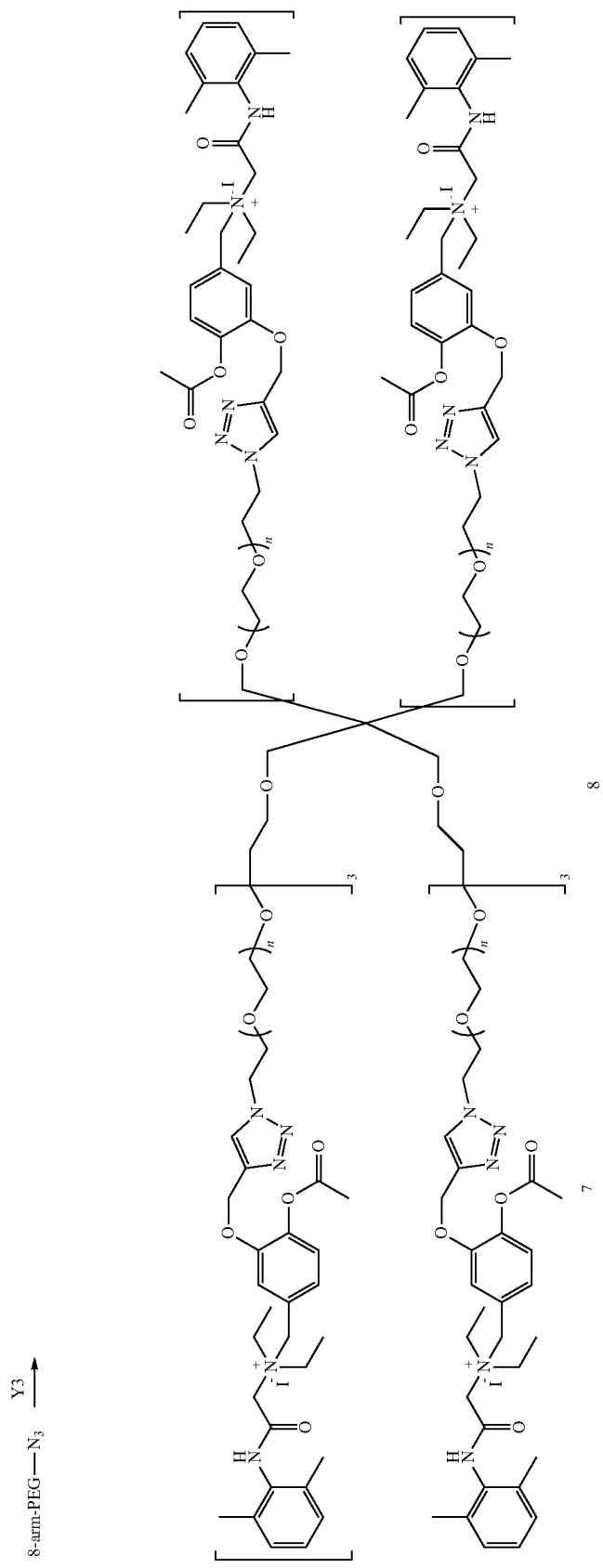

8-arm-PEG-N3 (20 K, 2 g, 0.1 mmol), compound Y3 (618.5 mg, 1 mmol), vitamin C (440 mg, 2.5 mmol) were added to N, N-dimethylformamide (20 mL), the resulting mixture was rapidly stirred to dissolve, then added with an aqueous solution (4.4 mL, 2.2 mL/g PEG) of copper sulfate pentahydrate (250 mg, 1 mmol), the resulting mixture was reacted at room temperature overnight and precipitated with isopropanol to give 1.7 g of product. 1H NMR: (CDCl3): 1H NMR: (CDCl3): 1.07 (m, 48H), 2.14 (s, 48H), 2.31 (s, 24H), 2.41 (m, 32H), 3.52 (s, 16H), 3.54 (m, 1800H), 3.79 (m, 16H), 3.92 (m, 16H), 4.53 (s, 16H), 4.82 (s, 16H), 5.22 (s, 16H), 6.90 (d, 8H), 7.09 (s, 8H), 7.28 (m, 24H), 7.69 (s, 8H), 10.27 (s, 8H).

Example 14 Synthesis of Quaternary Ammonium Salt of Bupivacaine (Y4)

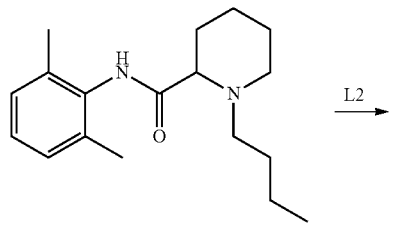

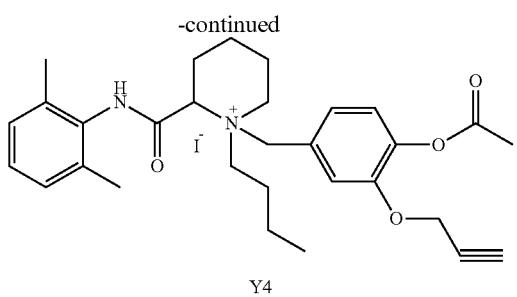

Bupivacaine (0.5 g, 1.7 mmol) and compound L2 (1.8 g, 3.2 mmol) were added to acetonitrile (20 mL) and reacted at 50° C. overnight. TLC monitoring showed that bupivacaine was reacted completely, and the reaction liquid was concentrated to give a crude product, which was purified by column chromatography to give 1.5 g of product Y4. 1H NMR: (CDCl3): 1.09 (m, 3H), 1.25 (m, 1H), 1.33 (m, 3H), 1.72 (m, 3H), 1.95 (m, 1H), 2.13 (s, 6H), 2.20 (m, 1H), 2.30 (s, 6H), 3.20 (m, 1H), 3.25 (m, 2H), 3.29 (m, 1H), 3.34 (s, 1H), 4.57 (s, 2H), 4.69 (s, 2H), 4.75 (s, 2H), 6.90 (d, 1H), 7.05 (d, 1H), 7.09 (d, 1H), 7.18 (m, 3H), 10.07 (s, 1H).

Example 15 Synthesis of Conjugate 9 of Bupivacaine (4-Arm-PEG-Bupivacaine, 10 K)

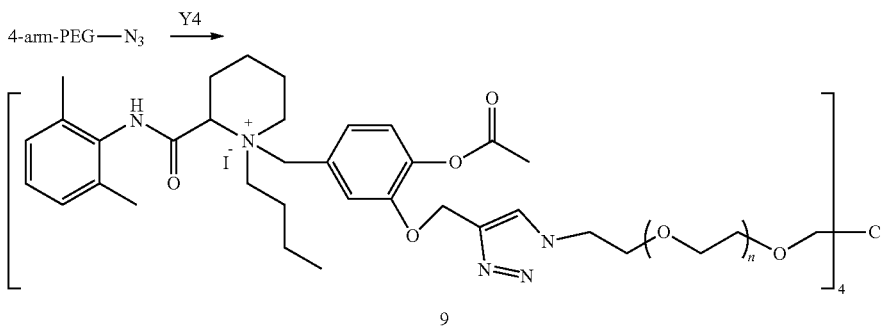

4-arm-PEG-N3 (10 K, 2 g, 0.2 mmol), compound Y4 (747.7 mg, 1 mmol), vitamin C (440 mg, 2.5 mmol) were added to N, N-dimethylformamide (20 mL), the resulting mixture was rapidly stirred to dissolve, then added with an aqueous solution (4.4 mL, 2.2 mL/g PEG) of copper sulfate pentahydrate (250 mg, 1 mmol), the resulting mixture was reacted at room temperature overnight and precipitated with isopropanol to give 1.8 g of product. 1H NMR: (CDCl3): 1.09 (m, 12H), 1.25 (m, 4H), 1.33 (m, 12H), 1.72 (m, 12H), 1.95 (m, 4H), 2.13 (s, 24H), 2.20 (m, 4H), 2.30 (s, 24H), 3.20 (m, 4H), 3.25 (m, 8H), 3.28 (m, 4H), 3.50 (s, 8H), 3.54 (m, 900H), 3.86 (m, 8H), 3.91 (m, 8H), 4.52 (s, 8H), 4.59 (s, 8H), 5.23 (s, 8H), 6.82 (d, 4H), 7.03 (d, 4H), 7.09 (s, 4H), 7.18 (m, 12H), 7.65 (s, 4H), 10.13 (s, 4H).

Example 16 Synthesis of Conjugate 10 of Bupivacaine (8-Arm-PEG-Bupivacaine, 20K)

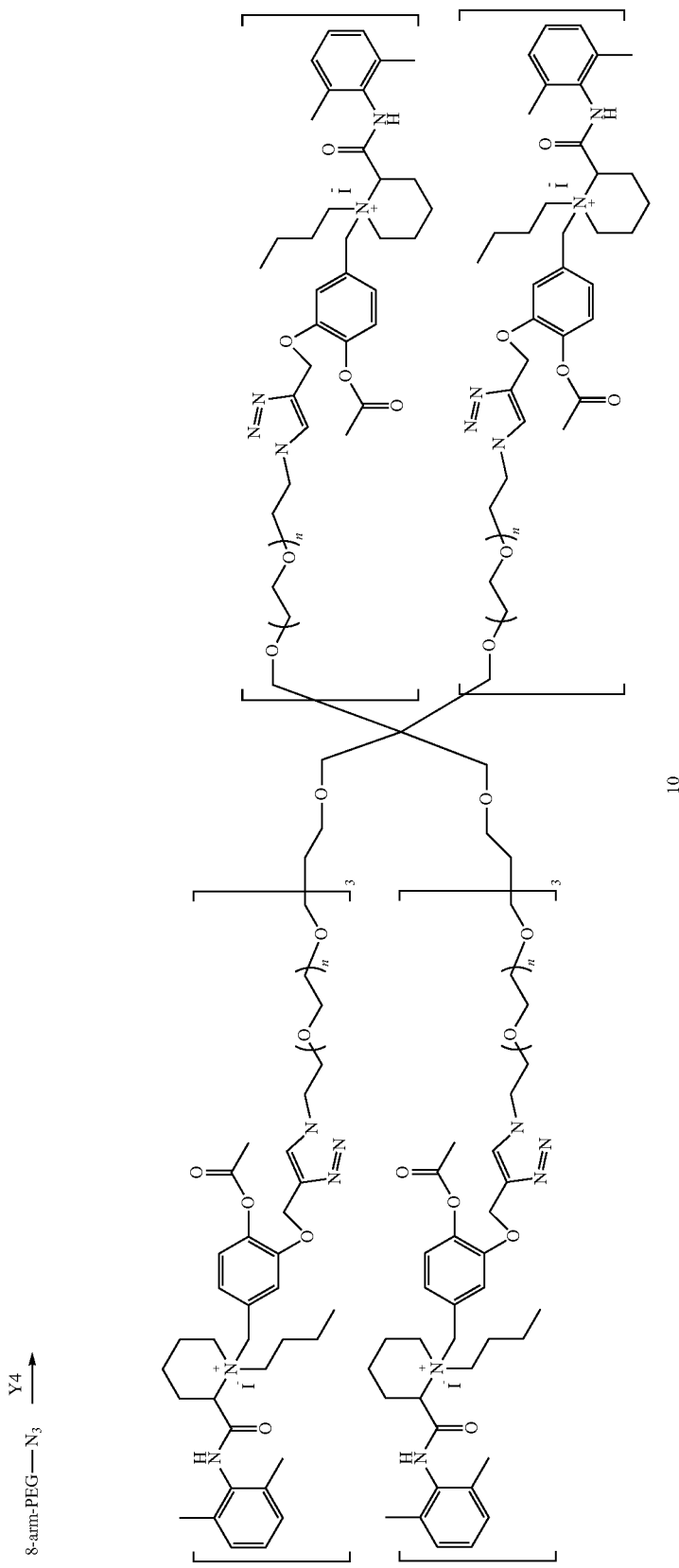

8-arm-PEG-N3 (20 K, 2 g, 0.1 mmol), compound Y2 (747.7 mg, 1 mmol), vitamin C (440 mg, 2.5 mmol) were added to N, N-dimethylformamide (20 mL), the resulting mixture was rapidly stirred to dissolve, then added with an aqueous solution 4.4 mL, 2.2 mL/g PEG) of copper sulfate pentahydrate (250 mg, 1 mmol), the resulting mixture was reacted at room temperature overnight and precipitated with isopropanol to give 1.6 g of product. 1H NMR: (CDCl3): 1H NMR: (CDCl3): 1.08 (m, 24H), 1.24 (m, 8H), 1.34 (m, 24H), 1.73 (m, 24H), 1.93 (m, 8H), 2.14 (s, 48H), 2.21 (m, 8H), 2.31 (s, 48H), 3.21 (m, 8H), 3.25 (m, 16H), 3.28 (m, 8H), 3.50 (s, 16H), 3.53 (m, 1800H), 3.85 (m, 16H), 3.92 (m, 16H), 4.53 (s, 16H), 4.59 (s, 16H), 5.22 (s, 16H), 6.81 (d, 8H), 7.05 (d, 8H), 7.09 (s, 8H), 7.19 (m, 24H), 7.67 (s, 8H), 10.12 (s, 8H).

Example 17 Study on the Efficacy of Compounds

1. Material

60 SD rats, male, with weight of 260-280 grams; lidocaine hydrochloride injection; bupivacaine hydrochloride injection; four-arm and eight-arm lidocaine and bupivacaine (2, 3, 5, and 6) injections.

2. Method 2.1. Grouping and Modeling

SD rats with normal pain threshold were randomly divided into 9 groups, with 6 rats in each group. The pain model was established with reference to the Brennan method, and the specific method was: fasting for 6 hours, fasting water for 1 hour before surgery, determining pain threshold by Von Frey method, then placing the rats into a closed anesthesia box, carrying out induced anesthesia with 1.5-2% isoflurane, when the animal consciousness disappeared, taking the animals out, disinfecting their right hind foot with iodophor, making an incision with a length of about 1 cm starting about 5 mm from proximal end of plantar and extending toward the toes; cutting the skin and fascia, elevating the plantar muscles with an ophthalmic forceps and longitudinally cutting (maintaining the starting and ending and attachment of the muscles intact); pressing to stop bleeding, before stitching the skin, injecting the animals in each group with 0.5 ml normal saline, 4 mg/kg bupivacaine hydrochloride, 10 mg/kg lidocaine hydrochloride injection, 4 mg/kg polyethylene glycol bupivacaine (counted by bupivacaine), and 10 mg/kg polyethylene glycol lidocaine (counted by lidocaine) in the incision, respectively; after the completion of administration, stitching the incision with 2-0 thin silk for 2 stitches. During the entire surgery, the rats were anesthetized with the same concentration of isoflurane through a mask.

2.2 Von Frey Test and Result Statistics

After the animals were awake and their state returned to normal (about 1 hour after surgery), the pain threshold was measured with Von Frey method. Then the pain thresholds of each group of animals were measured at the $3^{rd}$, $6^{th}$, $12^{th}$, $24^{th}$, $48^{th}$ and $72^{nd}$ hours after surgery, respectively. When the pain threshold was measured, the surgical foot of each model rat was stimulated by a filament with gradually increased force, and the paw withdrawal threshold (g) of animals was recorded, the measurement was repeated 2-3 times and the mean value was taken. The test results were analyzed by SPSS17.0. The number of the result was expressed in x±s. The comparison between groups was analyzed by one-way analysis of variance and P<0.05 meant that the differences were statistically significant. The experimental results are shown in Table 1 below.

TABLE 1

| Groups | Von Frey Hairs (g) | | | | | | | |
|---|---|---|---|---|---|---|---|---|
| | Basline | 1 h | 3 h | 6 h | 12 h | 24 h | 48 h | 72 h |
| Sham-operated group | 7.4 ± 0.7 | 7.5 ± 0.6 | 7.3 ± 0.7 | 7.8 ± 0.9 | 7.5 ± 0.8 | 7.2 ± 0.9 | 7.4 ± 0.6 | 7.5 ± 0.7 |
| Vehicle group | 7.4 ± 0.8 | 0.6 ± 0.2 | 0.7 ± 0.4 | 1.1 ± 0.3 | 1.1 ± 0.2 | 1.1 ± 0.5 | 2.0 ± 0.4 | 2.9 ± 0.6 |
| Lidocaine hydrochloride | 7.5 ± 0.8 | 6.6 ± 0.5 | 6.1 ± 0.4 | 4.0 ± 0.6 | 1.5 ± 0.4 | 1.4 ± 0.2 | — | — |
| Bupivacaine hydrochloride | 7.3 ± 0.7 | 4.3 ± 0.7 | 6.6 ± 0.4 | 5.3 ± 0.5 | 3.4 ± 0.9 | 1.7 ± 0.4 | — | — |
| 2 (4a-lidocaine) | 7.6 ± 0.7 | 4.8 ± 0.5 | 5.3 ± 0.6 | 4.1 ± 0.7 | 4.3 ± 0.4 | 2.7 ± 0.3 | 2.0 ± 0.5 | 2.4 ± 0.3 |
| 3 (8a-lidocaine) | 7.5 ± 0.7 | 4.2 ± 0.3 | 4.3 ± 0.6 | 3.8 ± 0.5 | 3.2 ± 0.4 | 2.2 ± 0.2 | 1.8 ± 0.4 | 3.1 ± 0.6 |
| 5 (4a-bupivacaine) | 7.3 ± 0.8 | 4.9 ± 0.3 | 5.8 ± 0.4 | 6.2 ± 0.5 | 6.1 ± 0.4 | 6.7 ± 0.8 | 5.4 ± 0.5 | 5.7 ± 0.4 |
| 6 (8a-bupivacaine) | 7.4 ± 0.7 | 3.6 ± 0.6 | 4.6 ± 0.5 | 4.9 ± 0.7 | 5.3 ± 0.6 | 4.8 ± 0.6 | 4.2 ± 0.4 | 3.9 ± 0.2 |

2.3 Discussion of the Results

From the results, it can be seen that bupivacaine hydrochloride takes effect more slowly than lidocaine hydrochloride, but has a relatively long duration, and after PEGylation, the two drugs have significantly prolonged duration, which have significant analgesic effect in 48-72 hours after surgery. Relatively speaking, the four-arm type drug has better analgesic intensity and duration of analgesia than that of eight-arm type drug.

The invention claimed is:

1. A conjugate of polyethylene glycol and anesthetic having the structure of formula (I):

$$\text{PEG-A-R}_0\text{-B} \qquad (I)$$

wherein, PEG is polyethylene glycol residue with a molecular weight of 1-100 KDa;

$R_0$ is a $C_{1-6}$ alkyl;

B is an anesthetic;

a quaternary ammonium salt with a structure of

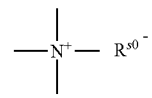

is formed at the linking position between B and $R_0$, $R^{s0-}$ is selected from the group consisting of F—, Cl—, Br—, I—, methanesulfonate, ethanesulfonate, benzenesulfonate, citrate, lactate, succinate, fumarate, glutamate, citrate, salicylate, and maleate;

and, A is a linking group selected from the group consisting of the structures shown by the following formula $A_1$ or $A_2$:

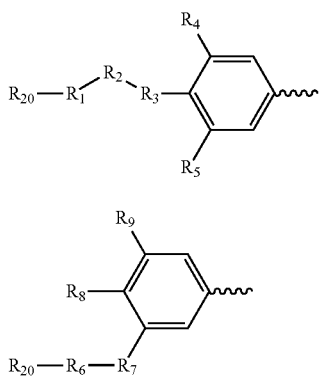

(A₁)

(II-1)

wherein m is an integer of 20-2000.

6. The conjugate of claim 5, wherein m is an integer of 200-1000.

7. The conjugate of claim 4, wherein the PEG is a 4-arm or 8-arm polyethylene glycol residue having the structures of formula (II-3) to formula (II-5):

(A₂)

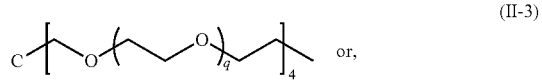
(II-3)

(II-4)

or,

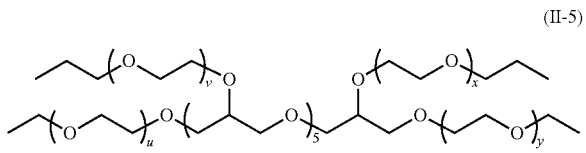
(II-5)

wherein, $R_1$ and $R_6$ are independently selected from $C_{1-6}$ alkyl, or $R_1$ and $R_6$ are independently selected from —(CH₂)ᵢNHCO(CH₂)ⱼ—, and —(CH₂)ᵢCONH(CH₂)ⱼ—, $R_2$ is selected from the group consisting of —C=O, —C=S, —O— or —S—;

$R_3$ and $R_7$ are independently selected from the group consisting of —O— or —S—;

$R_4$ or $R_5$ is independently selected from the group consisting of H, $C_{1-6}$ alkyl or halogen;

$R_8$ or $R_9$ is independently selected from the group consisting of H, $C_{1-6}$ alkyl or —O(C=O)(CH₂)ᵢCH₃;

i and j are integer independently selected from 0 to 6; and, $R_{20}$ is

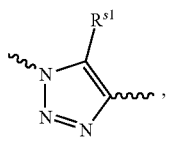, wherein, q is an integer selected from 5 to 500;

s, t, u, v, x, and y are integer independently selected from 2 to 250.

8. The conjugate of claim 7, wherein q is an integer selected from 50 to 250; and/or, s, t, u, v, x, and y are integer independently selected from 25 to 125.

9. The conjugate of claim 1, wherein the linking group A is selected from the group consisting of the structures shown in the following formulas A₃-A₆:

$R^{s1}$ is selected from the group consisting of H or $C_{1-6}$ alkyl.

2. The conjugate of claim 1, wherein the $R^{s0-}$ is selected from the group consisting of F—, Cl—, Br—, I—, methanesulfonate, ethanesulfonate, and benzenesulfonate; and/or, the $R_1$ and $R_6$ are independently selected from the group consisting of methyl, ethyl, or propyl; and/or, the $R_4$ or $R_5$ is independently selected from the group consisting of H, methyl or ethyl; and/or, the $R_8$ or $R_9$ is independently selected from the group consisting of H, methyl, ethyl, propyl, acetoxy, propionyloxy, and butyryloxy; and/or, the i and j are integer independently selected from 1, 2, or 3; and/or, the $R^{s1}$ is selected from the group consisting of H, methyl, ethyl or propyl.

3. The conjugate of claim 1, wherein the PEG has a molecular weight of 10 to 40 KDa.

4. The conjugate of claim 1, wherein the PEG is a linear, double-ended, Y-type, 4-arm, 6-arm or 8-arm polyethylene glycol residue.

5. The conjugate of claim 4, wherein the PEG is a linear polyethylene glycol residue having the structure of formula (II-1):

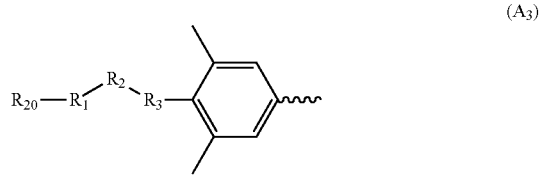
(A₃)

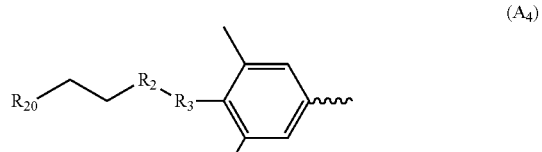
(A₄)

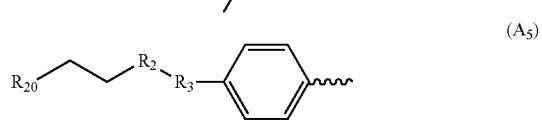
(A₅)

-continued

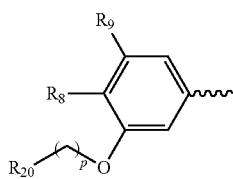
(A6)

wherein, $R_1$ is methyl, ethyl, propyl or —(CH$_2$)$_i$NHCO(CH$_2$)$_j$—, —(CH$_2$)$_i$CONH(CH$_2$)$_j$—;
$R_2$ is —C=O, —O— or —S—;
$R_3$ is —O— or —S—;
$R_8$ is acetoxy, propionyloxy or butyryloxy;
$R_9$ is H or methyl;
$R_{20}$ is

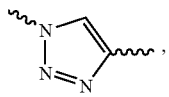

i and j are independently selected from 1, 2 or 3;
and, P is 1, 2 or 3.

10. The conjugate of claim 1, wherein the anesthetic is a local anesthetic of amides having the structure of formula (III):

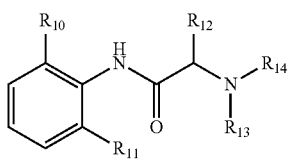
(III)

wherein, $R_{10}$ and $R_{11}$ are independently selected from the group consisting of H and C$_{1-6}$ alkyl;
and, $R_{12}$, $R_{13}$ and $R_{14}$ are independently selected from the group consisting of H and C$_{1-6}$ alkyl; or $R_{13}$ is selected from the group consisting of H and C$_{1-6}$ alkyl, N together with $R_{12}$ and $R_{14}$ forms a 5- to 8-membered ring.

11. The conjugate of claim 10, wherein $R_{10}$ and $R_{11}$ are independently selected from the group consisting of H, methyl, ethyl or propyl;
and, $R_{12}$, $R_{13}$ and $R_{14}$ are independently selected from the group consisting of H, methyl, ethyl, propyl or butyl; or $R_{13}$ is selected from the group consisting of H and C$_{1-6}$ alkyl, N together with $R_{12}$ and $R_{14}$ forms a 6-membered ring.

12. The conjugate of claim 10, wherein the anesthetic is lidocaine, prilocaine, bupivacaine, ropivacaine, mepivacaine or etidocaine.

13. The conjugate of claim 1, wherein the conjugate is selected from the group consisting of the structures shown in the formula (IV) to formula (X):

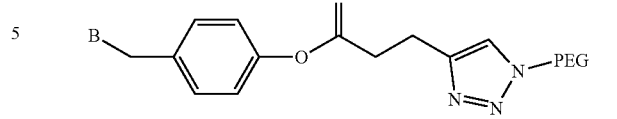
(IV)

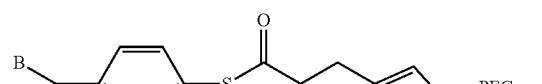
(V)

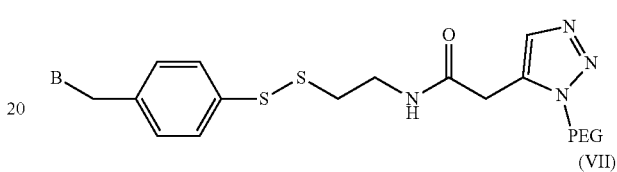
(VI)

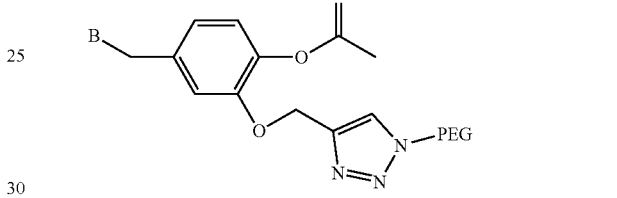
(VII)

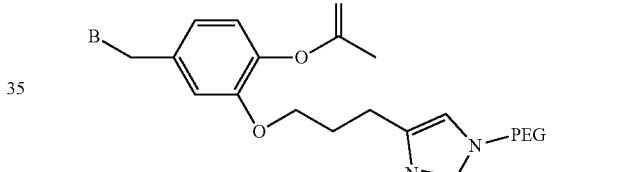
(VIII)

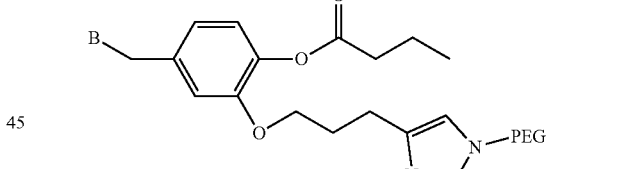
(IX)

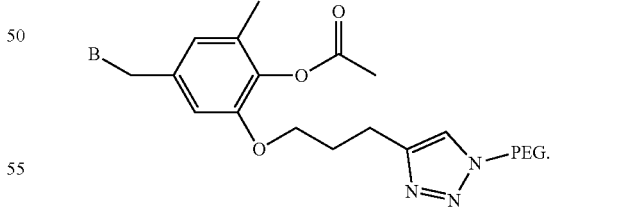
(X)

14. The conjugate of claim 13, wherein the PEG has a molecular weight of 10 to 40 KDa.

15. The conjugate of claim 14, wherein the PEG is a linear, double-ended, Y-type or multi-branched polyethylene glycol residue.

16. The conjugate of claim 11, wherein the conjugate is selected from the group consisting of the structures shown below:

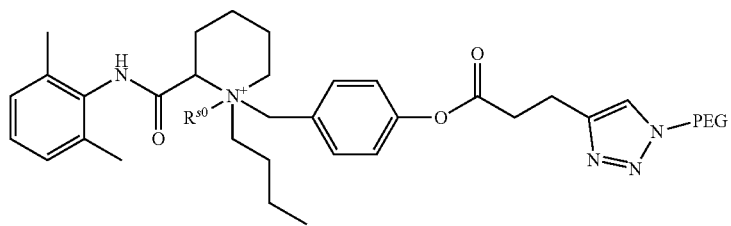
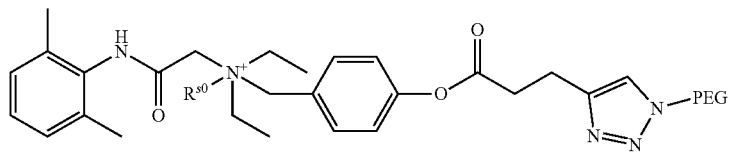
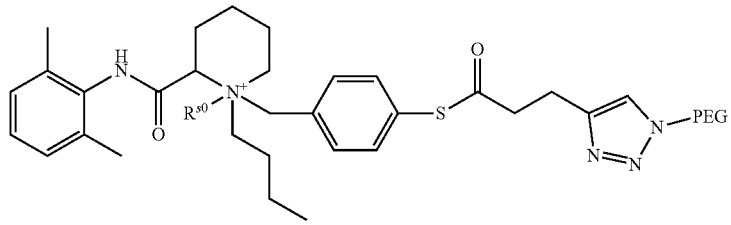
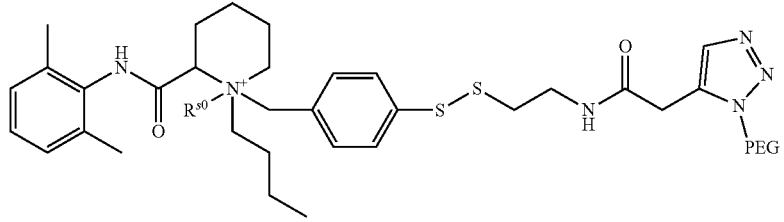
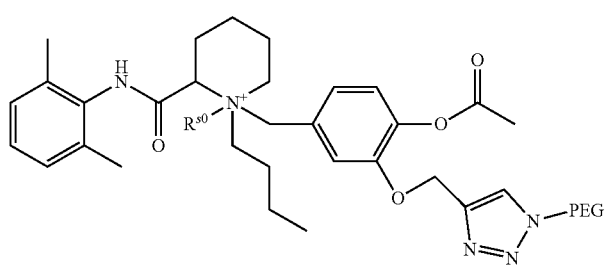
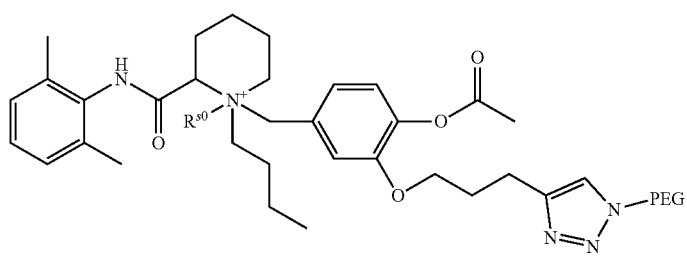
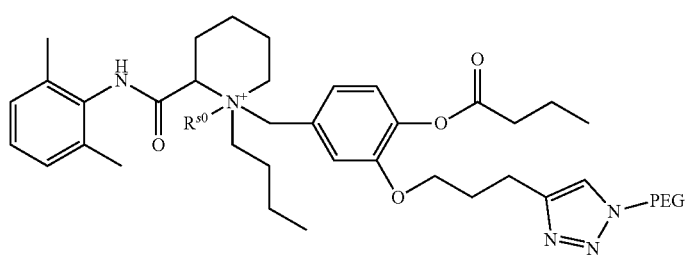

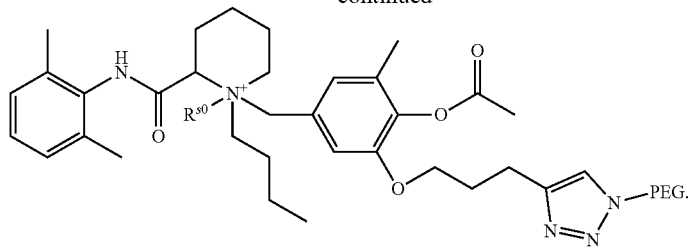
17. The conjugate of claim 1, wherein the conjugate is selected from the group consisting of the structures shown in the formula (XI) to formula (XXXI):
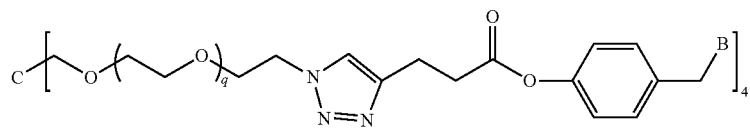
(XI)
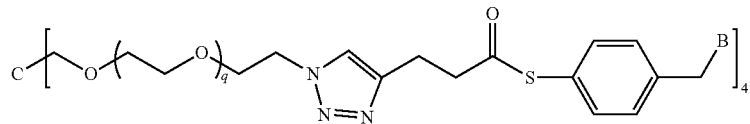
(XII)
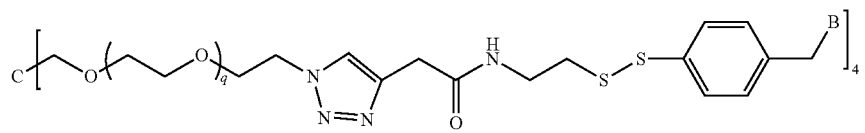
(XIII)
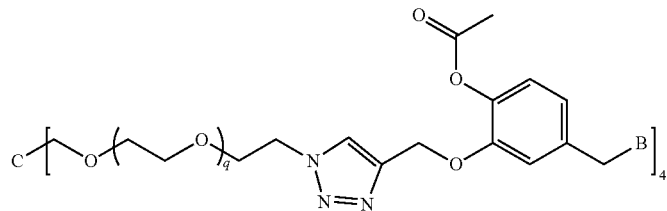
(XIV)
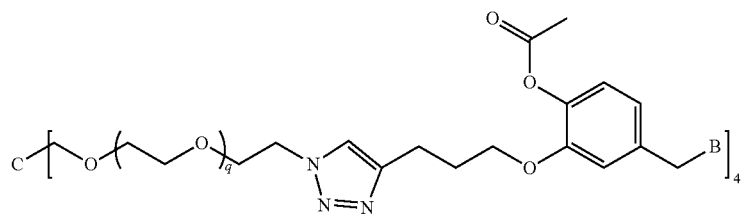
(XV)
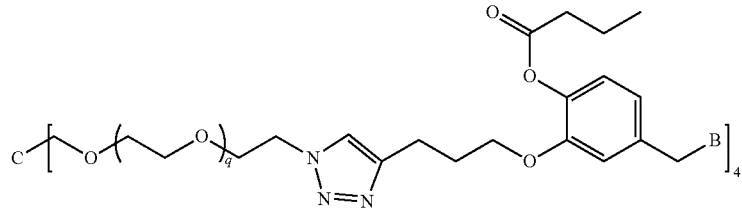
(XVI)

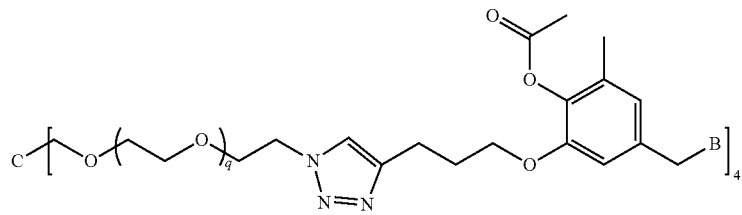
(XVII)
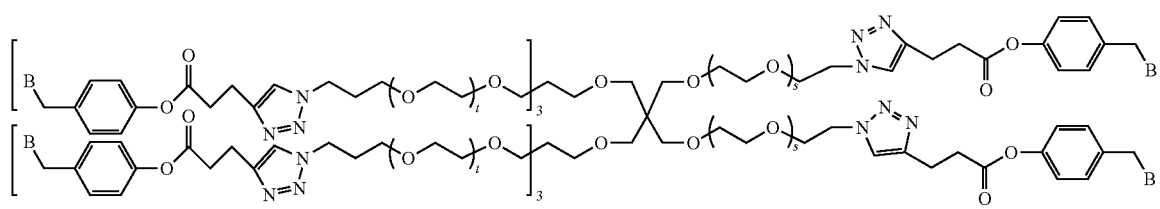
(XVIII)
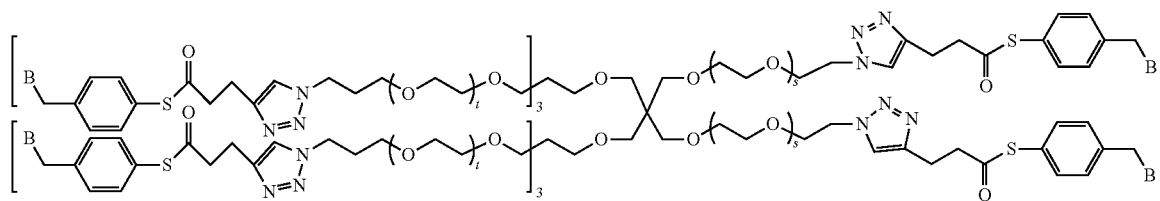
(XIX)
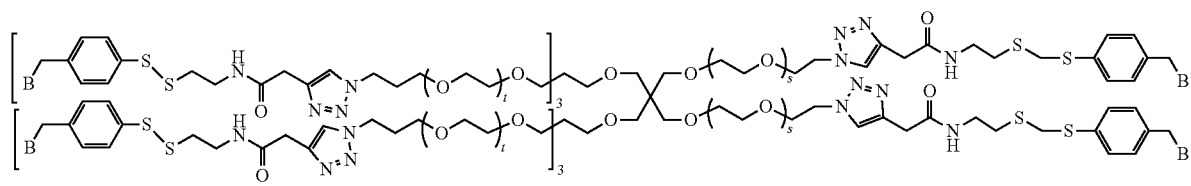
(XX)
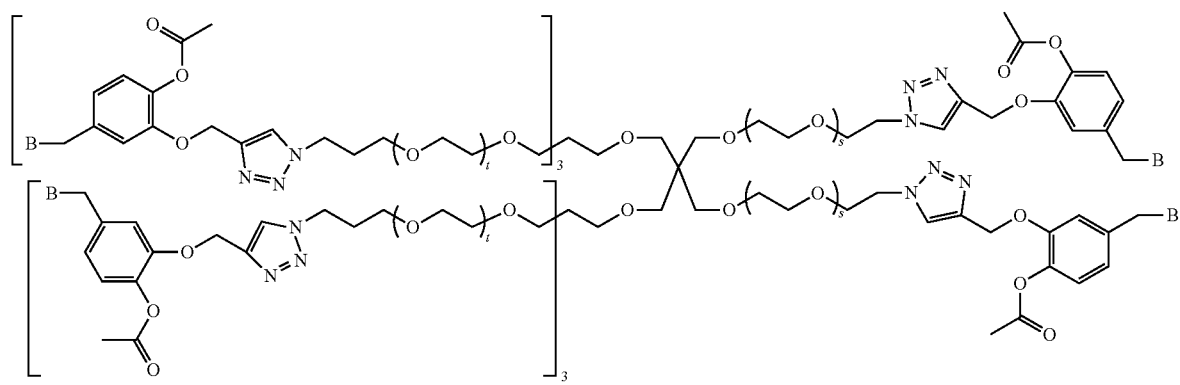
(XXI)

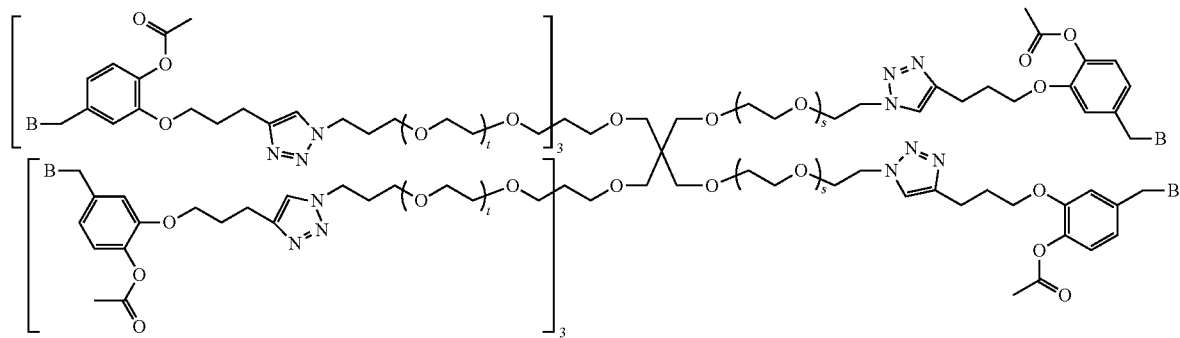
(XXII)
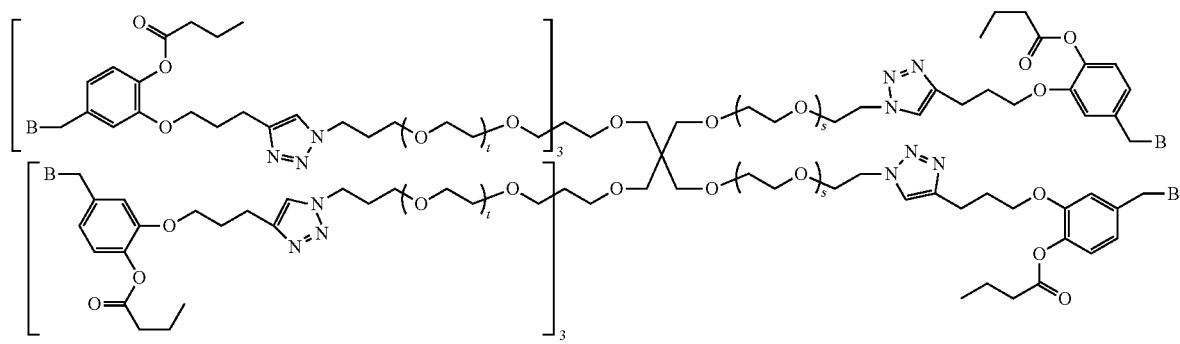
(XXIII)
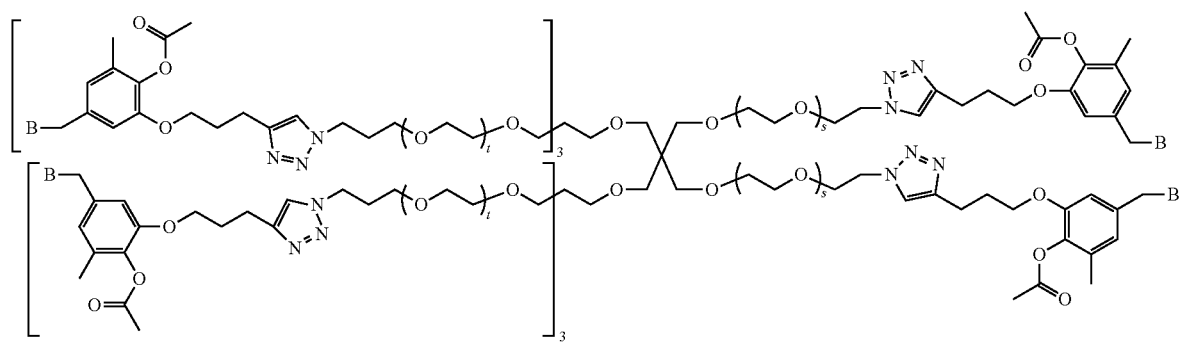
(XXIV)
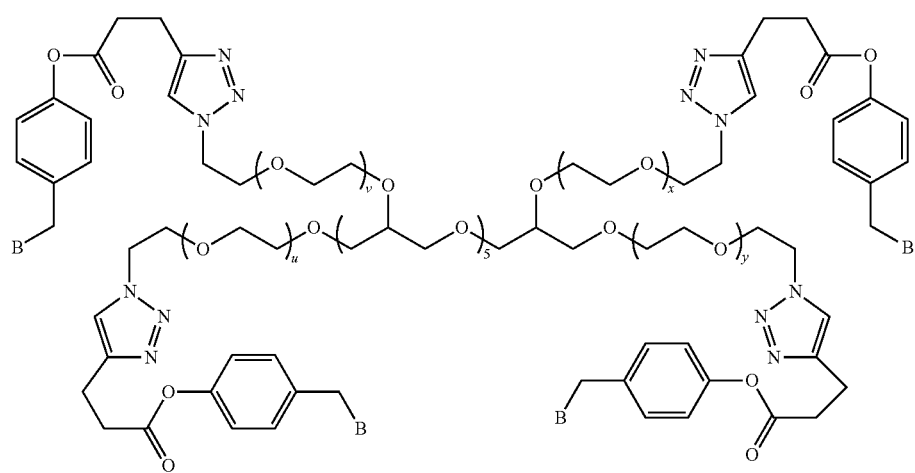
(XXV)

(XXVI)
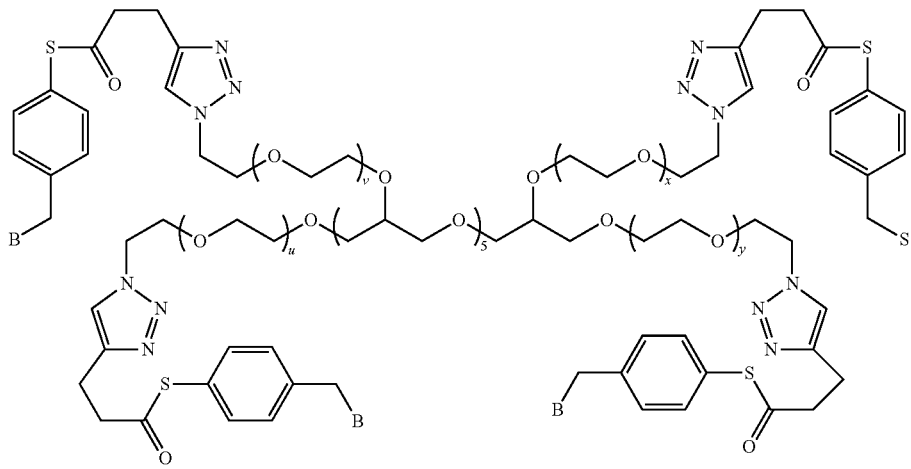
(XXVII)
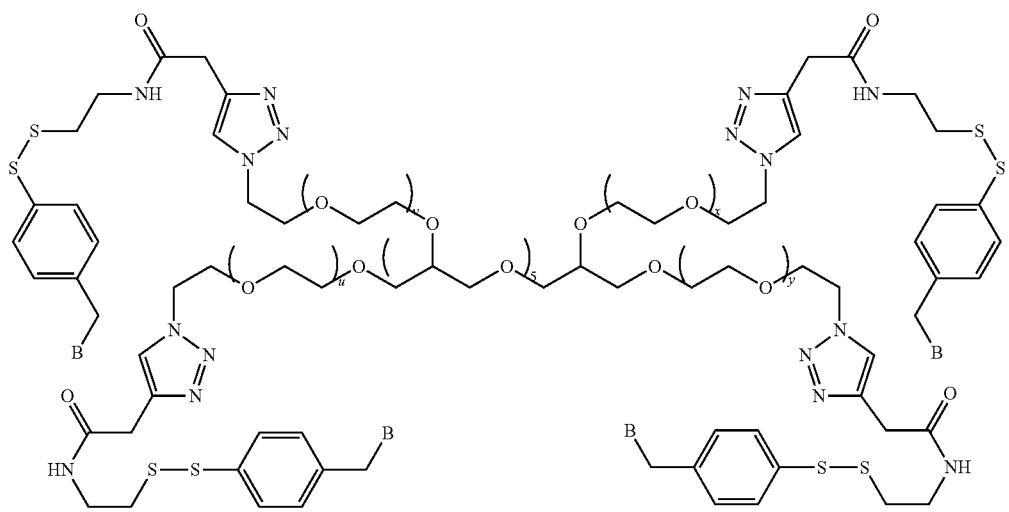
(XXVIII)
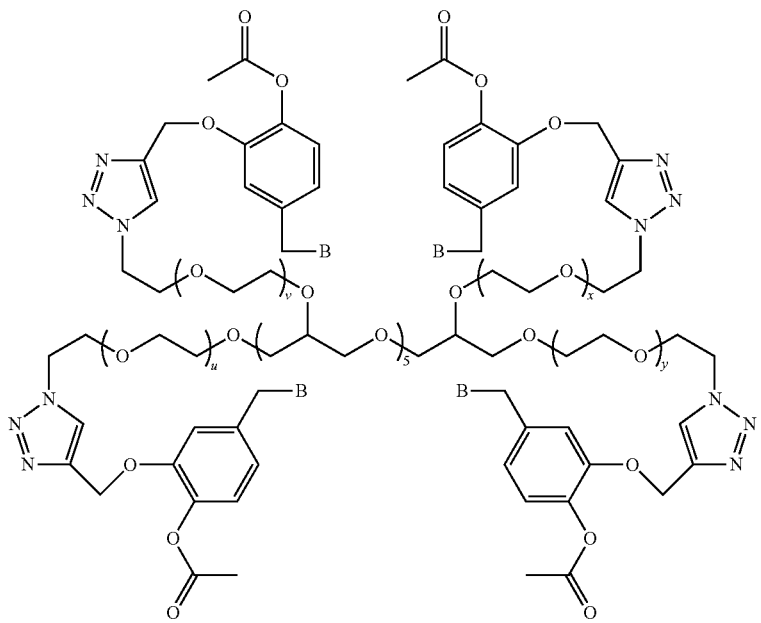

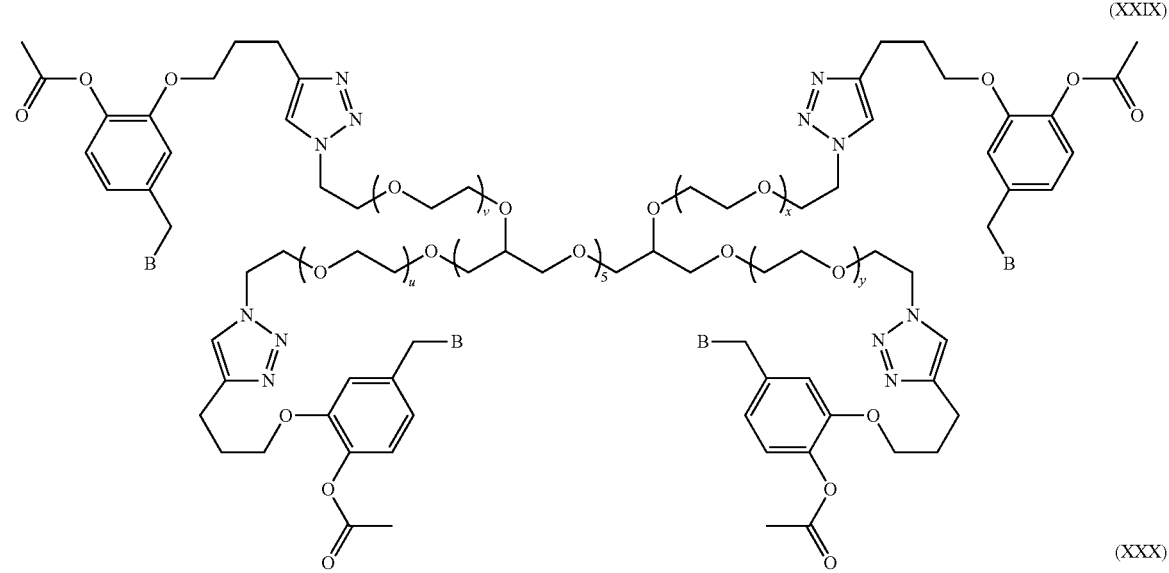
(XXIX)
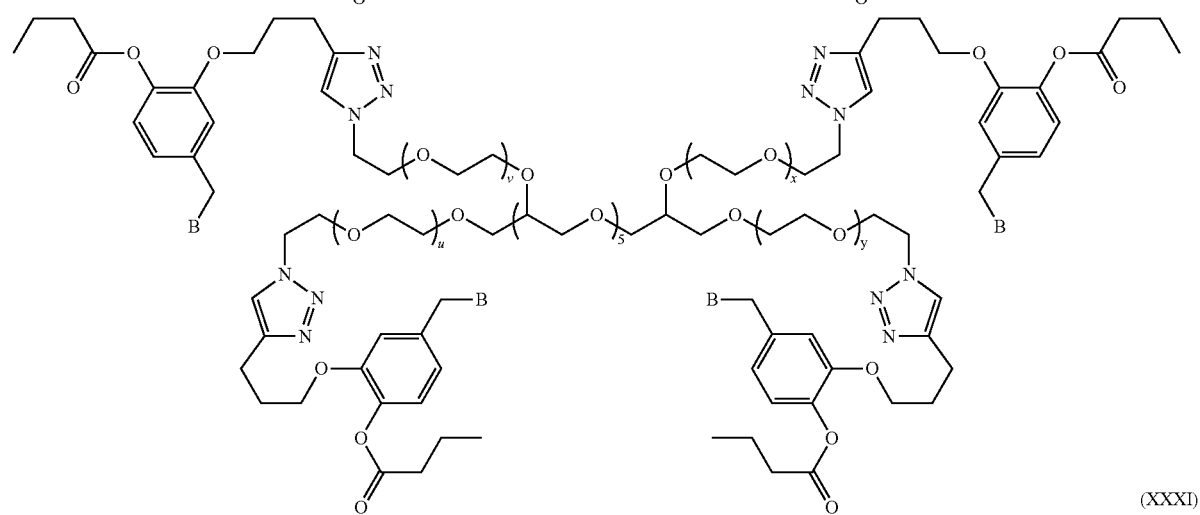
(XXX)
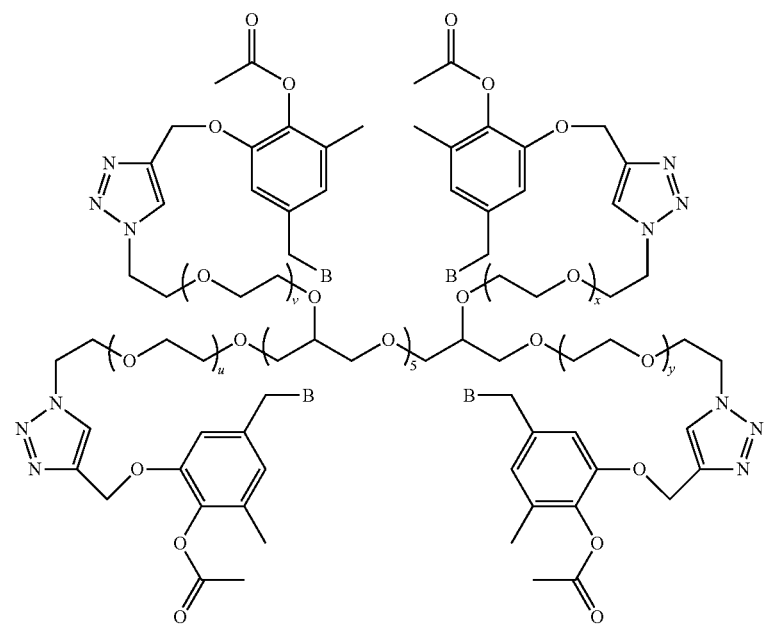
(XXXI)

wherein, a quaternary ammonium salt with a structure of $$-\underset{|}{\overset{|}{N^+}}-\ R^{s0-}$$

is formed at the linking position between B and —CH$_2$—, R$^{s0-}$ is selected from the group consisting of F—, Cl—, Br—, or I—, q is an integer selected from 5 to 500, and s, t, u, v, x, and y are integer independently selected from 2 to 250.

18. A method for analgesic or the treatment of chronic pain, comprising administering an effective amount of the conjugate of claim 1.

19. A preparation method of the conjugate of claim 1 comprising the following steps: (1) obtaining a linking group with one end group of alkynyl or azido at one end and one halogenated or sulfonated end group at one end with a structure represented by the following formula M$_1$ or M$_2$; (2) reacting the linking group obtained in step (1) with an anesthetic to form a quaternary ammonium salt; (3) reacting the alkynyl or azido of the quaternary ammonium salt obtained in step (2) with PEG modified with end group modified by azido or alkynyl to form the structure;

(M$_1$)

(M$_2$)

wherein:

PEG is polyethylene glycol residue with a molecular weight of 1-100 KDa;

n is an integer of 1-6, preferably 1, 2 or 3;

R$_{21}$ is selected from alkynyl or azido;

R$^{s0-}$ is selected from the group consisting of F—, Cl—, Br—, I—, methanesulfonate, ethanesulfonate, benzenesulfonate, citrate, lactate, succinate, fumarate, glutamate, citrate, salicylate, and maleate, preferably, R$^{s0-}$ is selected from the group consisting of F—, Cl—, Br—, I—, methanesulfonate, ethanesulfonate, and benzenesulfonate;

wherein, R$_1$ and R$_6$ are independently selected from C$_{1-6}$ alkyl, preferably methyl, ethyl, propyl, or R$_1$ and R$_6$ are independently selected from —(CH$_2$)$_i$NHCO(CH$_2$)$_j$—, and —(CH$_2$)$_i$CONH(CH$_2$)$_j$—, i and j are integer independently selected from 0 to 6, preferably 1, 2, or 3;

R$_2$ is selected from the group consisting of —C=O, —C=S, —O— or —S—;

R$_3$ and R$_7$ are independently selected from the group consisting of —O— or —S—;

R$_4$ or R$_5$ is independently selected from the group consisting of H, C$_{1-6}$ alkyl or halogen, preferably H, methyl or ethyl;

R$_8$ or R$_9$ is independently selected from the group consisting of H, C$_{1-6}$ alkyl or —O(C=O)(CH$_2$)$_i$CH$_3$, i is an integer of 0-6, preferably H, methyl, ethyl, propyl, acetoxy, propionyloxy, or butyryloxy;

and, the H atom of the alkynyl end group may be substituted with R$^{s1}$, R$^{s1}$ is selected from the group consisting of H or C$_{1-6}$ alkyl, preferably H, methyl, ethyl or propyl.

20. The preparation method of claim 19, wherein the linking group in step (1) is selected from the group consisting of the structures shown in M$_3$-M$_6$ below:

M$_3$

M$_4$

M$_5$

M$_6$ wherein:

R$_{21}$ is selected from the group consisting of alkynyl or azido;

R$^{s0-}$ is selected from the group consisting of F—, Cl—, Br—, and I—;

R$_1$ is methyl, ethyl, propyl or —(CH$_2$)$_i$NHCO(CH$_2$)$_j$—, —(CH$_2$)$_i$CONH(CH$_2$)$_j$—, i and j are independently selected from 1, 2 or 3;

R$_2$ is —C=O, —O— or —S—;

R$_3$ is —O— or —S—;

R$_8$ is acetoxy, propionyloxy or butyryloxy;

R$_9$ is H or methyl;

and, P is 1, 2 or 3.

* * * * *